(12) United States Patent
Phillips et al.

(10) Patent No.: US 11,724,090 B2
(45) Date of Patent: Aug. 15, 2023

(54) CANNULA, CANNULA SYSTEM AND BLOOD PUMP SYSTEM

(71) Applicant: Berlin Heart GmbH, Berlin (DE)

(72) Inventors: Daniel Phillips, Berlin (DE); Markus Stollin, Großbeeren (DE)

(73) Assignee: Berlin Heart GmbH, Berlin (DE)

( * ) Notice: Subject to any disclaimer, the term of this patent is extended or adjusted under 35 U.S.C. 154(b) by 580 days.

(21) Appl. No.: 16/768,465

(22) PCT Filed: May 18, 2018

(86) PCT No.: PCT/EP2018/063189
§ 371 (c)(1),
(2) Date: May 29, 2020

(87) PCT Pub. No.: WO2019/105597
PCT Pub. Date: Jun. 6, 2019

(65) Prior Publication Data
US 2020/0368413 A1 Nov. 26, 2020

(30) Foreign Application Priority Data
Dec. 1, 2017 (WO) .................. PCT/EP2017/081267

(51) Int. Cl.
*A61M 60/122* (2021.01)
*A61M 60/216* (2021.01)
(Continued)

(52) U.S. Cl.
CPC .......... *A61M 60/122* (2021.01); *A61M 39/00* (2013.01); *A61M 39/02* (2013.01);
(Continued)

(58) Field of Classification Search
CPC .............. A61M 60/122; A61M 60/859; A61M 60/178; A61M 60/216; A61M 39/00;
(Continued)

(56) References Cited

U.S. PATENT DOCUMENTS

| | | | |
|---|---|---|---|
| 9,821,099 B2* | 11/2017 | Miyakoshi | A61M 60/859 |
| 2008/0221469 A1* | 9/2008 | Shevchuk | F16L 33/23 96/10 |
| 2013/0060268 A1* | 3/2013 | Herrig | A61M 39/12 606/153 |

FOREIGN PATENT DOCUMENTS

| | | |
|---|---|---|
| DE | 202 14 608 U1 | 12/2002 |
| EP | 3 087 950 A1 | 11/2016 |

(Continued)

OTHER PUBLICATIONS

English translation of International Search Report, issued in International Application No. PCT/EP2018/063189, dated Aug. 16, 2018, pp. 1-3, European Patent Office, Rijswijk, Netherlands.
(Continued)

*Primary Examiner* — Dung T Ulsh
(74) *Attorney, Agent, or Firm* — Crowell & Moring LLP

(57) ABSTRACT

A cannula system is provided. The system may comprise: a cannula having a hose element having front and rear end regions, wherein a channel extends from the front end region to the rear end region, a hollow body having a front end region, and a connector which, in a connected state of the cannula system in which the front end region of the hollow body is introduced into the channel of the hose element, receives the front end region of the hose element and the front end region of the hollow body in an inner region of the connector. The connector may exert clamping forces on the front end region of the hose element and clamp the front end region of the hose element between the front end region of the hollow body and the connector. Also provided is a blood pump system including such a cannula system.

13 Claims, 21 Drawing Sheets

(51) Int. Cl.
    *A61M 60/178* (2021.01)
    *A61M 60/859* (2021.01)
    *A61M 39/00* (2006.01)
    *A61M 39/02* (2006.01)
    *A61M 39/10* (2006.01)
    *A61M 39/12* (2006.01)

(52) U.S. Cl.
    CPC ........ *A61M 39/0247* (2013.01); *A61M 39/10* (2013.01); *A61M 39/12* (2013.01); *A61M 60/178* (2021.01); *A61M 60/216* (2021.01); *A61M 60/859* (2021.01); *A61M 2039/0258* (2013.01); *A61M 2205/02* (2013.01)

(58) Field of Classification Search
    CPC .. A61M 39/02; A61M 39/0247; A61M 39/10; A61M 39/12; A61M 2039/0258
    See application file for complete search history.

(56) References Cited

FOREIGN PATENT DOCUMENTS

| | | |
|---|---|---|
| JP | 2011-177428 | 11/2013 |
| WO | WO 2007/103464 A2 | 9/2007 |
| WO | WO 2013/036643 A2 | 3/2013 |

OTHER PUBLICATIONS

English translation of International Search Report and Written Opinion, issued in International Application No. PCT/EP2017/081267, dated Feb. 6, 2018, pp. 1-8, European Patent Office, Rijswijk, Netherlands.

* cited by examiner

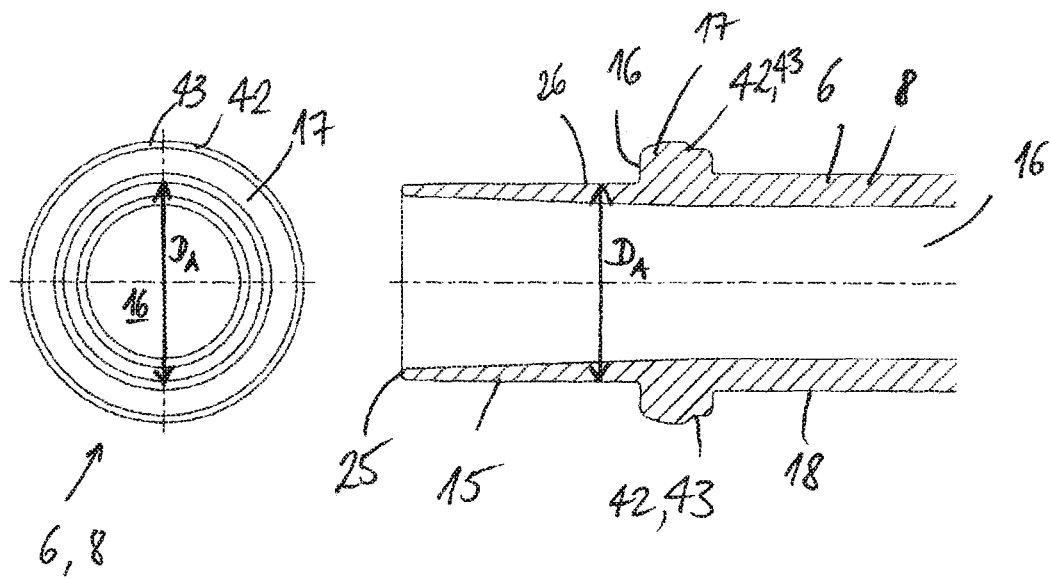
Fig. 7A
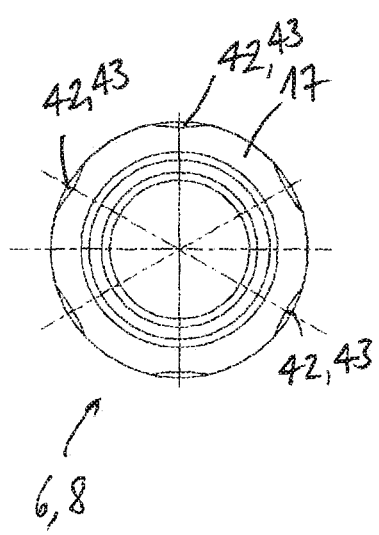 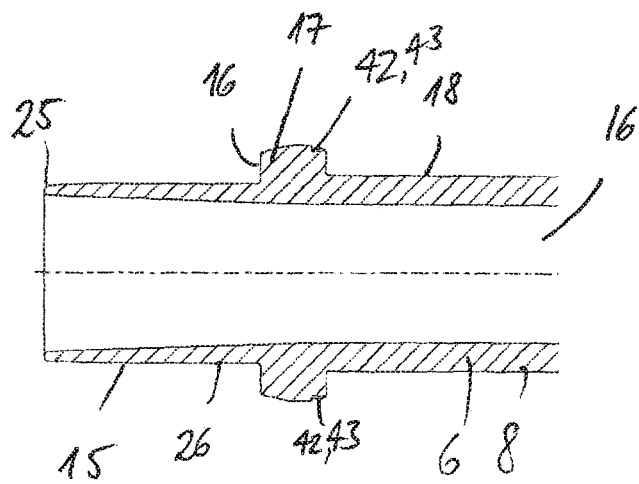
Fig. 7B

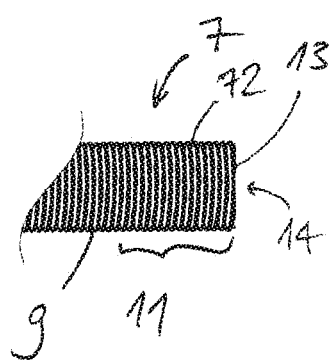
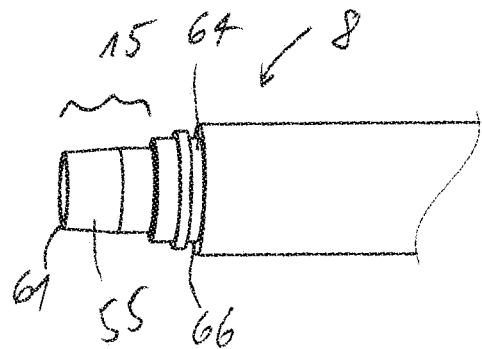
Fig. 11
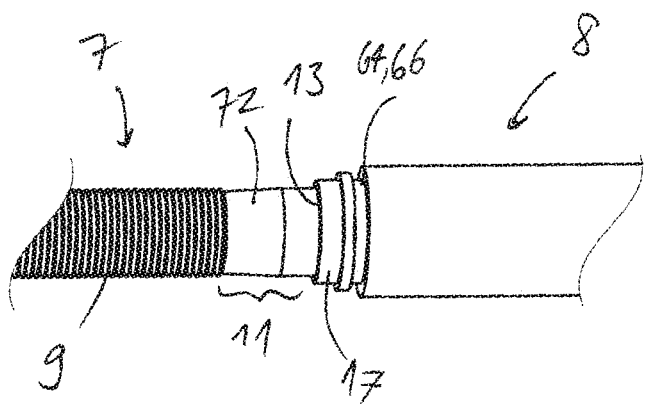
Fig. 12

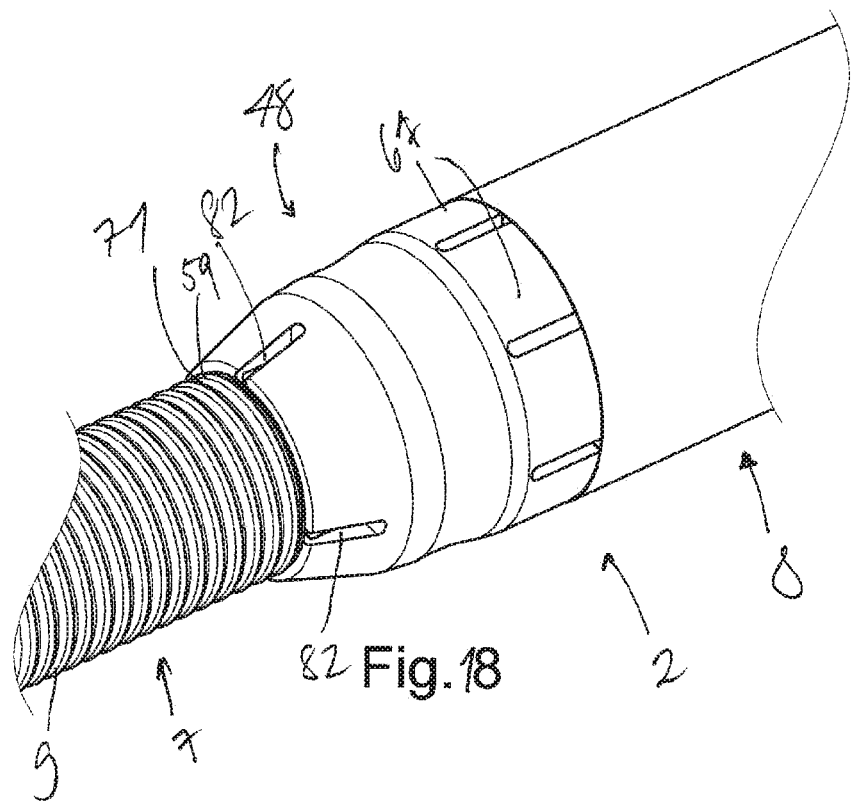
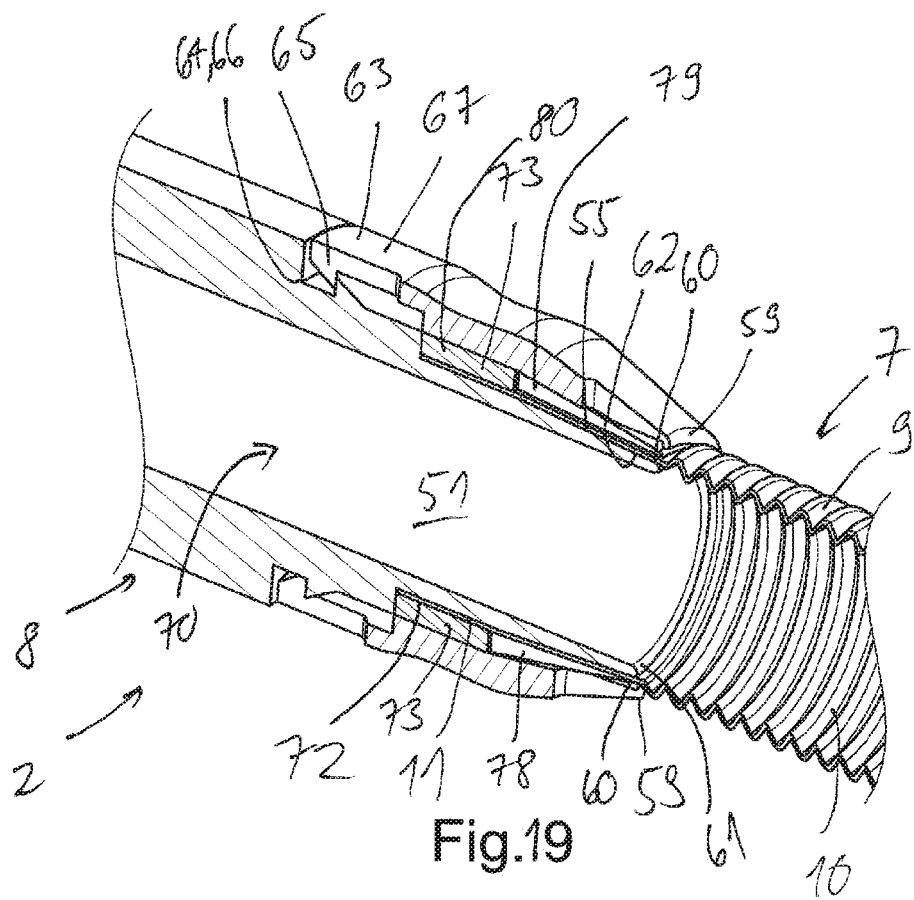

US 11,724,090 B2

CANNULA, CANNULA SYSTEM AND BLOOD PUMP SYSTEM

CROSS-REFERENCE TO RELATED APPLICATIONS

This application is a 371 nationalization of international patent application PCT/EP2018/063189 filed May 18, 2018, which claims priority under 35 USC § 119 to international patent application PCT/EP2017/081267 filed Dec. 1, 2017. The entire contents of each of the above-identified applications are hereby incorporated by reference.

TECHNICAL FIELD

The invention relates to a cannula for conducting a liquid, in particular blood. The invention further relates to a cannula system. The invention also relates to a blood pump system comprising such a cannula system.

BRIEF DESCRIPTION OF THE DRAWINGS

FIG. 7A shows a hollow body of the cannula system shown in FIG. 4A in a collapsed axial view and in a longitudinal sectional illustration;

FIG. 7B shows a hollow body of the cannula system shown in FIG. 4B in a collapsed axial view and in a longitudinal sectional illustration;

FIG. 11 shows a perspective illustration of a cannula and of a hollow body separated therefrom of a cannula system of the type proposed here;

FIG. 12 shows a perspective illustration of the cannula shown in FIG. 10, wherein the hollow body is pushed into the channel of the cannula;

FIG. 18 shows a perspective illustration of a further exemplary embodiment of a cannula system of the type proposed here in a connected state;

FIG. 19 shows a longitudinal section through the cannula system shown in FIG. 18 in the connected state;

FIG. 26 shows a perspective illustration of an exemplary embodiment of a cannula system of the type proposed here, wherein the connector of the cannula system is connected;

FIGS. 26B-D show further illustrations of the cannula system shown in

FIGS. 27B-D show further illustrations of the cannula system shown in

FIG. 27A; and

FIG. 27D shows a longitudinal section through the cannula system shown in FIG. 27C.

DETAILED DESCRIPTION

Figure 1:
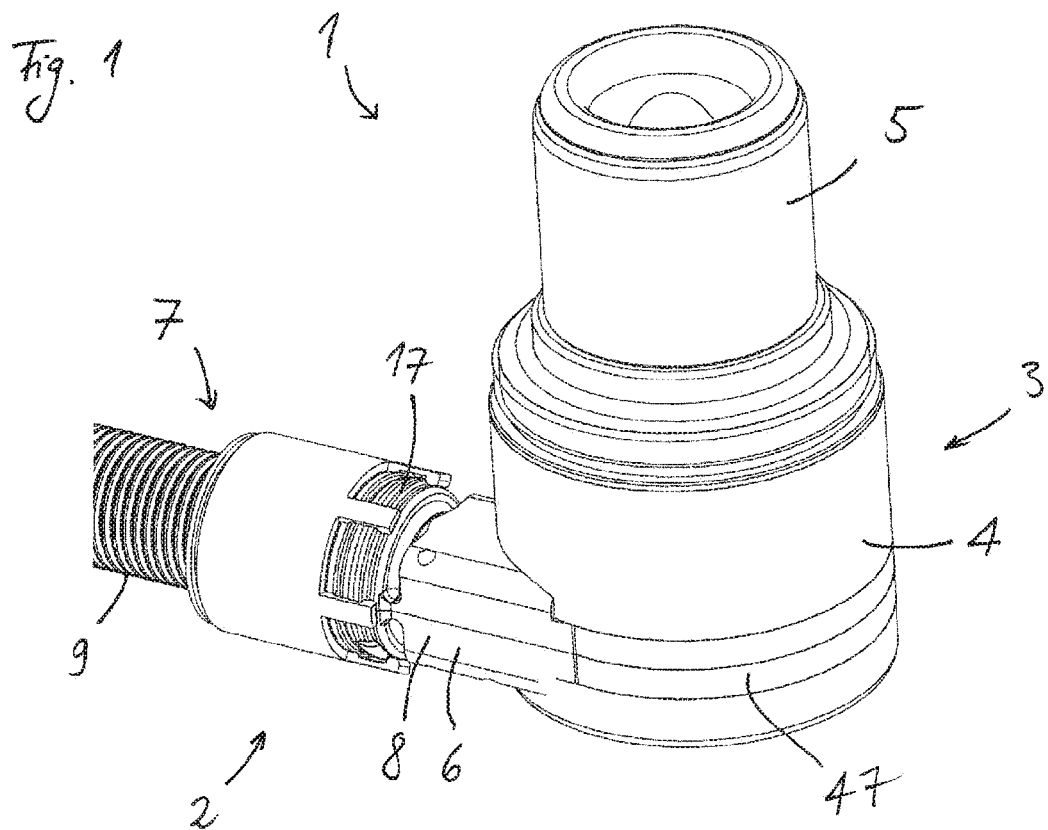
FIG. 1 shows a perspective illustration of a blood pump system of the type proposed here.

Cannulas are used in many fields of technology for conducting liquids. For example, cannulas are used in medical technology for conducting endogenous liquids such as blood. A cannula can be configured, for example, as an implantable vascular prosthesis and serve as a replacement for a natural blood vessel.

In many applications, such as in the case of vascular prostheses, it is important to be able to establish a secure connection between the cannula and another hollow body, such as a pump outlet of a blood pump, as quickly and as easily as possible.

It is thus the object of the present invention to propose a cannula system that enables a connection between a cannula and a hollow body that is as easy, fast and secure as possible. Preferably, it is to be made possible to establish this connection purely manually to the greatest extent possible, that is, without the use of tool to the greatest extent possible. Furthermore, a corresponding blood pump system comprising such a cannula system is to be proposed. Moreover, a cannula that can be connected to another hollow body as easily, quickly and securely as possible, and a corresponding cannula system comprising such a cannula, and a blood pump system comprising such a cannula system are desirable.

This object is achieved by cannula systems and blood pump systems described in the following description and the figures.

In addition to this cannula system, moreover a special cannula is proposed, which is characterized by a tension ring. In addition, cannula systems and blood pump systems comprising this special cannula are proposed. Exemplary embodiments that relate to this special cannula comprising a tension ring are likewise described in the following description, see in particular the "aspects" hereafter. Moreover, several of the figures show exemplary embodiments including this special cannula comprising a tension ring.

The cannula systems proposed here (with or without tension ring), for conducting a liquid, in particular blood, comprise a cannula including a hose element which has a front end region and a rear end region, wherein a channel extends from the front end region of the hose element to the rear end region of the hose element through the hose element. The cannula system further comprises a hollow body, and in particular a tube or a further hose element, wherein the hollow body comprises a front end region that can be inserted into the channel of the hose element through a front inlet opening of the channel.

The cannula system can comprise a connector, for example, which is designed to detachably connect the cannula or the hose element to the hollow body. In a connected state of the cannula system, for instance the front end region of the hollow body is inserted into the channel of the hose element of the cannula. The front end region of the hose element and the front end region of the hollow body are received in an interior region of the connector. The interior region can be a cavity formed by the connector, for example.

In the connected state of the cannula system, the front end region of the hollow body and the connector are configured, for example, to exert clamping forces (on both sides) on the front end region of the hose element and, in this way, clamp the front end region of the hose element between the front end region of the hollow body and the connector, so that undesired separation of the cannula or of the hose element from the hollow body, for example due to axial tensile forces, can be avoided. By suitably configuring the (radially) outer surface of the front end region of the hollow body and a (radially) inner surface of the connector, which (radially) circumscribes the interior region or the cavity of the connector, it is possible to accordingly predefine the clamping forces. Typically, the clamping forces also depend on the wall thickness of the front end region of the hose element and on further parameters, such as the elasticity, the compliance and the strength of the materials of which the hollow body, the connector and the hose element are made.

For example, the connector comprises a base body, which can have a sleeve-shaped or collar-shaped configuration, for example. The base body surrounds the interior region or the cavity of the connector and has a (radially) inner surface, which defines or (radially) circumscribes the interior region (cavity) of the connector. The inner surface can be contoured, as will be described in greater detail hereafter. The base body can have a single-piece design, or a two-piece or multi-piece design. For example, the base body can be formed by two half shells, which will be described hereafter. The base body can include one or more axial slots, which can each be disposed, for example, in axial end regions of the base body. In this way, a radial flexibility of the base body may be increased in these end regions, or detent arms of the connector may be formed, as will be described hereafter. If the base body has a one-piece design, the base body typically does not include any slots that extend across the entire axial length of the base body.

In some exemplary embodiments, the connector comprises two half shells, which can form the above-described base body, for example, and at least one joint that pivotably connects the two half shells to one another. The at least one joint can be formed by at least one hinge, for example. The two half shells can be pivoted, for example, about a (first) pivot axis formed by the at least one joint into an open configuration and into a closed configuration. The two half shells are configured, for example, to surround the interior region of the connector in the closed configuration, and to exert clamping forces on the front end region of the hose element in the connected state of the cannula system. In the open configuration, the two half shells can be pivoted apart from one another so as to define a (for example lateral) opening. It may, for example, be provided that, in particular when the two half shells and the hollow body are designed as two units which are detachable from one another as described below, the front end region of the hose element of the cannula and the front end region of the hollow body which is inserted into the channel can be pushed from the outside between the two half shells through this (lateral) opening. In some exemplary embodiments, in which the two half shells are fixedly (but movably) connected to the hollow body, it may for example be provided that the hollow body is inserted into the channel of the hose element and thereafter the two half shells are pivoted relative to the hollow body and the hose element (for example about the aforementioned pivot axis and/or the further pivot axis described hereafter) until the two half shells receive and/or enclose the front end regions of the hollow body and the hose element between themselves. Thereafter, it is possible, for example, to first place the one of the half shells onto the front end region of the hose element and the inserted front end region of the hollow body or brought into contact with it and thereafter, by pivoting the other half shell (for example about the (first) pivot axis), to bring also this other half shell in contact with the front end region of the hose element or place this other half shell thereon. The placing and/or bringing into contact of the two half shells on/with the front end region of the hose element and the pushed-in front end region of the hollow body may, in some exemplary embodiments, also take place simultaneously, for example by simultaneously pivoting the two half shells about the (first) axis. By further compression of the two half shells, this pivoting movement (about the (first) pivot axis) can be continued until, ultimately, the closed configuration of the half shells is achieved, and the above-described clamping forces are generated, so that ultimately the connected state of the cannula system is achieved. The connected state can thus be achieved without axial displacement of the connector, so that advantageously creasing of the hose element can be prevented or at least reduced. Moreover, an improved visual inspection of the hose element during connection is possible.

The hollow body on the one hand and the two half shells of the connector on the other hand may, for example, be designed as two independent, i.e. two detachable (or detachably connected to one another) units. In this case, the two half shells of the connector may be detachably connected to the hollow body, for example during the establishment of a connected state of the cannula system, as described above. Typically, the detachable connection of the two half shells is established manually, that is, without using tools, and may typically also be released manually (and nondestructively), for example when suspending the connected state of the cannula system.

Alternatively, however, it is also possible for the hollow body to be fixedly connected to the two half shells of the connector, that is to form a unit with the two half shells of the connector. In this case, typically the two half shell cannot be separated from the connector nondestructively or without using tools. In this way, an unintentional separation of the half shells from the connector or their getting lost, for example, may be avoided, in particular before or during the connection of a hollow body with the hose element or during release of this connection.

For example, the two half shells may be fixedly connected to the hollow body via the at least one joint, for example via the first joint described hereafter and second joint of the at least one joint. Additionally, or alternatively, the two half shells may also be fixedly connected to the hollow body via the at least one further joint described hereafter.

A fixed connected shall generally be understood to mean that releasing the connection is not possible nondestructively or not purely manually, without using a tool. However, due to the pivotability of the half shells with respect to one another and relative to the hollow body, the fixed connection described here, via the at least one joint or the at least one further joint described hereafter, is a movable connection.

In some exemplary embodiments, the at least one joint comprises a first joint and a second joint. For example, the first joint may be arranged on a first side of the hollow body and the second joint may be arranged on second side of the hollow body opposite to the first side of the hollow body. For example, the joint may comprise a first pin which is fixedly connected to the hollow body on the first side of the hollow body and is oriented parallel to the pivot axis of the at least one joint. The two half shells may each have a first opening through each of which the first pin extends in sections. Accordingly, the second may comprise a second pin which is fixedly connected to the hollow body on the second side of the hollow body and is oriented parallel to the pivot axis. The half shells may each have a second opening through each of which the second pin extends in sections. The first pin is rotatably mounted in the first openings. Accordingly, the second pin is also rotatably mounted in the second openings and thus allow for the described pivoting movements of the half shells about the first pivot axis. For example, the first pin and the second pin may be fixedly and rigidly connected to the hollow body, e.g. integrally.

In this and alternative exemplary embodiments it may be provided the (first) pivot axis of the at least one joint extends within a plane which is oriented essentially perpendicular to the longitudinal axis of the hollow body or perpendicular to the longitudinal axis of the hose element (In the connected state of the cannula system, the longitudinal axis of the hollow body typically extends parallel to the longitudinal axis of the channel of the hose element) It is thus in particular possible for the (first) pivot axis to be oriented essentially perpendicular to the longitudinal axis of the hollow body or (in the connected state) perpendicular to the longitudinal axis of the channel of the hose element. When the two half shells are pivoted apart, the described perpendicular orientation of the (first) pivot axis allows for the hollow body to be particularly accessible and visible, for example in order to be able to insert the hollow body into the hose element as easily as possible.

Alternatively, however, it may also be provided that the first pivot axis to be oriented essentially parallel to the longitudinal axis of the hollow body or (in the connected state) essentially parallel to the longitudinal axis of the channel of the hose element.

Essentially parallel is intended to correspond to an angle of, for example, between 170° and 190°, preferably of 180°. Essentially perpendicular is intended to correspond to an angle of, for example, between 80° and 100°, preferably of 90°.

The orientation of the (first) pivot axis relative to the hollow body or to its longitudinal axis may, for example, be fixed, in particular in the instances of the essentially perpendicular orientation and the essentially parallel orientation of the first pivot axis. To this end, it may be provided that the at least one joint (i.e., the first joint and the second joint described above, for instance) be directly connected to the hollow body.

As already mentioned above, the connector, in some exemplary embodiments, comprises at least one further joint which forms at least one further pivot axis which is different to the pivot axis of the at least one joint. For example, the two half shells may be fixedly connected to the hollow body via the at least one further joint and be pivotable relative to the hollow body about the at least one further pivot axis. In some embodiment examples, the at least one further pivot axis comprises exactly one further joint and exactly one further pivot axis. For example, the at least one further pivot axis may extend within a plane which is oriented essentially perpendicular to a longitudinal axis of the hollow body. For example, the pivot axis of the at least one joint may be oriented essentially perpendicular to the at least one further pivot axis of the at least one further joint.

In some exemplary embodiments, the at least one further joint can be moved between a first position and a second position by pivoting the half shells about the at least one further pivot axis. It may, for example, be provided that in the first position, the pivot axis of the at least one joint is oriented essentially parallel to the longitudinal axis of the hollow body. Additionally, or alternatively, it may be provided that in the second position, the pivot axis of the at least one joint is oriented essentially perpendicular to the longitudinal axis of the hollow body. In the second position of the at least one joint, the half shells are typically pivoted away from the hollow body such that it is freely accessible, whereby it is clearly visible and particularly easy to insert into the hose element. After the insertion, the at least one joint may be pivoted into the first position and the two half shells may be closed in order to established a connected state of the cannula system. In the connected state, the (first) pivot axis may be oriented essentially parallel to the longitudinal axis of the hollow body or essentially parallel to the longitudinal axis of the channel of the hose element, respectively.

In some exemplary embodiments, the at least one further (second) pivot axis is different from the (first) pivot axis so that the two half shells are pivotable about the first pivot axis and additionally also about the further or second pivot axis different therefrom. In this case, the two half shells are typically pivotable together relative to the hollow body about the at least one further or second pivot axis. In this case, the first joint and thus also the first pivot axis is typically (also) pivoted about the at least one further or second pivot axis, as in the exemplary embodiment described above. Pivoting movements about the first pivot axis may then, for example, be carried out without simultaneously carrying out pivoting movements about the second pivoting axis. Typically, it is also possible to carry out pivoting movements about the second pivot axis without simultaneously carrying out pivoting movements about the first pivoting axis.

The at least one joint may, for example, be connected to the hollow body via the at least one further joint (instead of being directly connected). In some exemplary embodiments, the at least one joint and thus also its (first) pivot axis are also moved by pivoting the two half shells relative to the hollow body about the (second) pivot axis via the at least one further joint. The orientation of the (second) pivot axis of the at least one further joint relative to the hollow body may, for example, be fixed, for instance by way of a direct connection of the at least one further joint to the hollow body. The at least one further joint can comprise at least one hinge, for example. One or more (for example two) joints of the at least one joint may be connected to the hollow body in a fixed, integral, or form-locked manner, for example.

In some exemplary embodiments, the at least one joint and/or the at least one further joint comprise at least a sleeve which receives a pin of the respective joint in sections and rotatably mounts it. The respective sleeve may be fixedly and rigidly connected either to the hollow body, to the first half shell, or to the second half shell. The respective joint may comprise a further sleeve which also receives and rotatably mount said pin in sections. The pin extends along the first or the second pivot axis, for example.

The at least one further (second) joint may, for example, have two sleeves which are each fixedly and rigidly connected to the connector. A pin extends, in each case in sections, through these sleeves and may be rotatably or non-rotatably mounted in them. The pin extends along the further (second) pivot axis. For example, the at least one (first) joint also has a pin which at one end of this pin is connected to the pin of the further (second) joint typically rigidly or rotatably around the pin of the second joint. In this example, the (first) joint as well as the two half shells is pivotable about the further (second) pivot axis, for example from the first position described above into the second position, and vice versa, by rotating the pin of the further (second) joint or by rotating the pin of the first joint about the pin of the further (second) joint.

The connector may have a securing sleeve which may be axially movable, relative to the base body or relative to two half shells of the connector, between a first position and a second position. The securing sleeve may, for example, be designed to receive the base body or the two half shells of the connector in the connected state of the cannula system, when the securing sleeve is in the second position. The securing sleeve may be dimensioned such that the securing sleeve stabilizes the two half shells in the closed configuration, when the securing sleeve is in the second position. The securing sleeve may have an inner contour, for example in the shape of an internal thread. The hollow body may have a corresponding outer contour, for example in the shape of a corresponding outer thread which is engaged with the inner thread of the securing sleeve. It may, for example, be provided that the securing sleeve can be moved back and forth between the first and second positions described above by rotating it via said thread.

The connector can comprise a locking device configured to hold the two half shells in the closed configuration. The locking device can, for example, comprise one or more detent elements, for example one detent element on the one half shell and a corresponding mating detent element on the other half shell. The at least one detent element can be configured to engage in the closed configuration of the half shells, for example when the two half shells are pivoted from the open configuration into the closed configuration.

The connector can comprise a clamping sleeve. The clamping sleeve can be made of an elastic material, for example a metallic material, such as titanium or a titanium alloy or stainless steel, or a polymer, such as a silicone. The clamping sleeve can be slotted along the entire axial length thereof, that is, include a longitudinal slot extending across the entire axial length of the clamping sleeve. The clamping sleeve is typically disposed in the interior region of the connector and configured, in the connected state of the cannula system, to enclose the front end region of the hose element and exert a clamping force of the connector on the front end region of the hose element. For example, the clamping sleeve can be configured to transmit a clamping force generated by the base body of the connector onto the front end region of the hose element. In addition, or as an alternative, the clamping sleeve can be configured to partially or completely induce the clamping force itself based on elastic properties. For example, the connector can comprise a wedge element, wherein the wedge element and the clamping sleeve can be moved relative to one another between a preloaded configuration and a released configuration. In the preloaded configuration, the wedge element is pushed into a slot (into the above-described longitudinal slot, for example) of the clamping sleeve, and the clamping sleeve is (elastically) preloaded and radially expanded by the wedge element. In the released configuration, the clamping sleeve is not preloaded and expanded by the wedge element. The wedge element and the clamping sleeve can be moved from the preloaded configuration into the released configuration when the cannula system is to be transferred into the connected state, in which the clamping sleeve generates the described clamping forces in the released configuration. In the preloaded expanded state, the clamping sleeve typically has a smallest inside diameter which is greater than a largest outside diameter of the front end region of the hose element, even if the hollow body is inserted therein. In this way, the clamping sleeve thus expanded is axially displaceable with respect to the front end region of the hose element up to a desired end position, and can be released in this end position for the generation of the clamping forces.

The connector can comprise an operating element which can be moved between a first position and a second position and forms an outer operating surface of the connector, which can be manually operated by a user so as to move the operating element between the first and second positions. The wedge element can be moved by a movement of the operating element. For this purpose, the operating element can be coupled to the wedge element, for example via an accordingly configured connecting member. The wedge element and the clamping sleeve are in the preloaded configuration, for example, when the operating element is in the first position. The wedge element and the clamping sleeve are in the released configuration, for example, when the operating element is in the second position.

The connector can include a region that is configured, in the connected state of the cannula system, to push an axial section of the hose element, which typically abuts the front end region of the hose element, radially inwardly against a foremost edge of the front edge region of the hollow body. The region of the connector can be formed, for example, by the front or rear end region of the base body of the connector. This may be slotted, as described above. Pushing, for example, can prevent liquid, such as blood, from being able to penetrate between the outer surface of the hollow body and the inner surface of the hose element resting thereon. In this way, for example in the case of blood, the risk of thrombi can be reduced.

The connector can include a front opening and a rear opening, which can be formed, for example, by the base body of the connector and each form an access to the interior region of the connector. In a force-free basic state of the hose element or of the cannula, the cannula, or at least the hose element of the cannula, can have a largest outside diameter which is smaller than a smallest inside diameter of the front opening, than a smallest inside diameter of the rear opening, and than a smallest inside diameter of the interior region of the connector. In this way, a free axial displaceability of the connector or of the base body thereof relative to the hose element or relative to the cannula can be achieved, provided the hollow body is not pushed in. It may be provided that, with further axial displacement contact occurs, in the front end region when the hollow body is inserted therein as described, between the outer surface of the front end region of the hose element and an inner surface of the connector or of another element, which is disposed radially between the inner surface of the base body and the outer surface of the front end region of the hose element (for example, of the subsequent flexible element), so that ultimately the described clamping forces are generated by further axial displacement. For this purpose, for example, an outside diameter of the front end region of the hollow body can increase from the foremost edge toward the rear (that is, in a direction toward the rear end of the hollow body).

The connector can comprise at least one connecting element, and the hollow body can also comprise at least one connecting element. The connecting elements can be configured, for example, to establish a detachable connection to the at least one connecting element of the connector in the connected state of the cannula system, for example so as to prevent undesirable axial displacement of the connector relative to the hollow body, for example by way of form fit and/or force fit between these connecting elements. For example, the at least one connecting element of the connector can comprise at least one radially inwardly directed protrusion. Moreover, the at least one connecting element of the hollow body can comprise at least one receiving region for the at least one protrusion of the connector. By mutual latching engagement, for example, a relative axial displacement of the connector and the hollow body can be blocked. It is also possible that the at least one connecting element of the connector comprises at least one detent arm, which includes the radially inwardly directed protrusion. The hollow body can, in turn, include a corresponding receptacle for such protrusions provided on detent arms. For example, the at least one connecting element of the connector can comprise a thread, and the at least one connecting element of the hollow body can comprise a mating thread for the thread of the connector.

In one exemplary embodiment, the connector includes at least one protrusion, which protrudes radially into the interior region and is configured to transmit at least a portion of the clamping forces onto the front end region of the hose element. This protrusion can form part of the base body of the connector, for example. The at least one protrusion can comprise at least one ridge, for example. The at least one ridge can, for example, extend partially or completely circumferentially around the interior region or extend in an axial direction. The at least one protrusion can taper radially inwardly or have a radially inwardly narrowing shape. In this way, it is possible to introduce the clamping forces in a localized manner into the hose element, thereby intensifying the clamping action. It is also possible for the at least one protrusion to penetrate into the material of the hose element, whereby a particularly stable connection is achieved.

The cannula system can comprise a flexible element, which is designed to abut the front end region of the hose element within the interior region of the connector in the connected state of the cannula system, and to transmit at least a portion of the clamping forces onto the front end region of the hose element. For example, the flexible element can be disposed radially outside the hose element so as to transmit clamping forces from portions of the connector located further to the radial outside, such as of the base body, inwardly onto the hose element. This can, in particular, be provided when the hollow body is made of a hard material. As an alternative, the flexible element can be disposed radially inside the hose element so as to transmit clamping forces originating from the hollow body onto the hose element. It may be provided that the flexible element deforms in some regions given the flexibility thereof and, for example, conforms to abutting surfaces of the hose element, of the hollow body or of the connector, or of the base body thereof, when the clamping forces are applied thereto. The deformations can thus, for example, effectuate an improved sealing action of the connection between the hose element and the hollow body or contribute to compensating better for tolerance deviations of the hollow body, of the hose element and/or of the connector. For example, the flexible element can be made of a compliant material, for example the compliant material being or comprising a polymer, such as an elastomer or a silicone.

For example, the flexible element can be configured, in the connected state of the cannula system, to rest against an inner surface of the front end region of the hose element in a planar manner, and to transmit at least a portion of the clamping force exerted by the front end region of the hollow body onto the front end region of the hose element. For example, the flexible element can be a portion or a subregion of the front end region of the hollow body, such as a radially outer casing of the hollow body. For example, the front end region of the hollow body can comprise a reinforcing sleeve, which is made, for example, of a preferably strong material, for example of a metallic material, such as stainless steel or titanium or a titanium alloy. The reinforcing sleeve is disposed radially inside the flexible element, for example. The reinforcing sleeve can be embedded in a material of the hollow body, for example, which can be soft and flexible. The reinforcing sleeve absorbs the clamping force introduced from radially outside and thus forms a counter bearing for the connector, for example.

For example, the flexible element can be configured, in the connected state of the cannula system, to rest against a (radially) outer surface of the front end region of the hose element in a planar manner, and to transmit at least a portion of the clamping force, exerted by the connector, onto the front end region of the hose element.

Due to the (radially) inner surface of the connector (which may be formed, for example, by the above-described base body of the connector) and the (radially) outer surface of the front end region of the hose element, an intermediate space may be formed, for example, in the connected state of the cannula system. This gap can be an annular gap at least in some sections. For example, the described flexible element can be configured to be disposed in this gap.

For example, the flexible element can be a sleeve that is detachable from the cannula, from the hollow body and from the connector and displaceable along the hose element. The sleeve is configured, for example, to completely or at least partially receive the front end region of the hose element therein when the front end region of the hollow body is inserted into the channel of the hose element. The cannula, or at least the hose element of the cannula, in a (force-free) basic state of the hose element or of the cannula, then has a largest outside diameter which is not greater than (that is, equal to or smaller than) a smallest inside diameter of the sleeve when the sleeve is likewise in the force-free basic state thereof or, as an alternative, if the sleeve is the above-described clamping sleeve, is preloaded and expanded, for example by means of the above-described wedge element. For example, in the connected state of the cannula system, the sleeve can be compressed by clamping forces of the connector acting from the outside radially to the inside, so that the inside diameter of the sleeve is reduced, and the sleeve rests against the hose element, transmitting the clamping forces thereto. As an alternative, in the case of the clamping sleeve, the clamping forces can be generated by the clamping sleeve itself (in the released state).

For example, an inside diameter and/or an outside diameter of the sleeve can decrease from a front end of the sleeve facing the hollow body toward a rear end of the sleeve facing the hose element. For example, the sleeve can be conically shaped or comprise a conically shaped region. The sleeve can include at least one axial slot, which typically, however, does not extend completely, but only partially across an axial extension of the sleeve. The sleeve then includes at least one non-slotted axial sub-segment.

As was already mentioned above, the cannula of the cannula system (with or without tension ring) for conducting a liquid, in particular an endogenous liquid such as blood, typically comprises a hose element including a front end region and a rear end region. The hose element defines in the interior thereof a channel for conducting the liquid. The channel extends axially through the hose element from the front end region of the hose element to the rear end region of the hose element. Typically, the channel extends from a foremost end (of the front end region) of the hose element to a rearmost end (of the rear end region) of the hose element.

The front end region of the hose element typically defines a receiving region for a hollow body to which the cannula is to be connected, such as the hollow body already described above. This hollow body, which is an integral part of the cannula system proposed here (with or without tension ring), is typically configured so as to be pushable into the channel through a front inlet opening of the channel, as will be described hereafter, for example. The front inlet opening of the channel is also referred to hereafter as the front opening of the channel. The front opening of the channel is typically located at the above-described foremost end of the hose element.

A corresponding connection to a further hollow body can also apply to the rear end region of the hose element. As an alternative, however, it may also be provided that the rear end region of the hose element is connected to a blood vessel, such as by suturing to the blood vessel or in another manner.

Here and hereafter, "axial" shall mean along the respective longitudinal extension of an element (for example, of the hose element or of the hollow body). Correspondingly, "radial" shall mean perpendicular to the longitudinal extension of the respective element. Moreover, accordingly, terms such as "at the front", "in front of", "front", "foremost" or "at the rear", "behind", "rear", "rearmost" and the like each refer to an arrangement in the axial direction, that is, along the respective longitudinal extension of an element.

Typically, the hose element is made of a soft and/or flexible material. For example, the hose element can be made of a graft material and/or may comprise, for example, a textile tubular carrier structure, as will be described in greater detail hereafter.

For example, the cannula can comprise reinforcing elements for the hose element, which can be used, for example, to strengthen the hose element and/or stabilize the shape thereof, for example so as to prevent undesirable bending of the hose element to the greatest extent possible. For example, spiral-shaped reinforcing elements may be used as reinforcing elements, which extend around the hose element or at least the channel in a spiral-shaped manner, for example. The reinforcing elements can be fixedly connected to the hose element, for example. For example, the reinforcing elements can be sewn or adhesively bonded to the hose element or be embedded into the material of the hose element. However, it is also possible that the cannula overall, or at least in the front end region of the cannula or of the hose element, does not comprise any reinforcing elements for the hose element. In particular, it may be provided that the cannula does not comprise any spiral-shaped reinforcing elements, for example no reinforcing elements that extend around the hose element and/or the channel in a spiral-shaped manner. For example, it may be provided that the cannula overall, or at least in the front end region of the cannula or of the hose element, does not comprise any reinforcing elements that are fixedly connected to the hose element or that are embedded into the material of the hose element (if necessary, in addition to a textile carrier structure of the hose element, if present).

For example, the cannula can comprise tensioning elements for the hose element, which are used, for example, to tension the material of the hose element in the radial direction and/or in the axial direction. The tensioning elements can be fixedly connected to the hose element, for example. For example, the tensioning elements can be sewn or adhesively bonded to the hose element or be embedded into the material of the hose element. The tension ring described hereafter may be used as a tensioning element, for example. However, it may also be provided that the cannula overall, or at least in the front end region of the cannula or of the hose element, does not comprise any such tensioning elements, and in particular does not comprise any tensioning elements fixedly connected to the hose element, that is, in particular, not the tension ring described hereafter.

The cannula can thus have a particularly simple design. For example, it may be provided, as was described above, that the cannula overall, or at least a front end region of the cannula, does not comprise any further elements, such as reinforcing elements or tensioning elements for the hose element, in addition to the front end region of the hose element. For example, it may be provided that the cannula overall, or at least a front end region of the cannula, is formed completely or partially by the hose element or by the front end region thereof. For example, at least a foremost edge of the cannula, which circumscribes the front inlet opening of the channel, can be formed completely or partially by the front end region or the foremost edge of the hose element. For example, the front end region of the hose element can be made exclusively of the material of the hose element, for example of a graft material (see hereafter). In particular, the front opening of the hose element or the foremost edge of the hose element defining the opening can thus be made exclusively of the material of the hose element, thus, for example, of a graft material. For example, the front end region of the cannula can be made of the material of the hose element, for example the graft material. The mechanical properties and the dimensions of the front end region of the cannula, and in particular the strength and the inside diameter, can thus agree with the corresponding properties and dimensions of the front end region of the hose element.

For example, the graft material can comprise a textile carrier structure, which is made, for example, of a woven fabric, for example of a polyester woven fabric. The textile carrier structure of the graft material can have a tubular configuration. The textile carrier structure can comprise a coating, by way of which the textile carrier structure can be sealed, for example. This coating can be made of gelatin, for example, or another biocompatible or hemocompatible material.

In a particularly simple example, the front end region of the cannula is formed completely by the front end region of the hose element, and thus does not comprise any tensioning elements and does not comprise any reinforcing elements that are fixedly connected to the front end region of the hose element. Moreover, the front end region of the hose element is made of a graft material. The graft material is formed by a tubular textile carrier structure, which is provided with a sealing coating.

The foremost edge of the hose element can have been created, for example, in that the hose element has previously been shortened at the front end thereof by cutting. In the simplest case, the front edge can thus be a cut edge of the hose element or a cut surface through the hose element.

For example, in the connected state of the cannula system, the graft material of the hose element can directly abut a (radially) outer surface of the hollow body. This (radially) outer surface of the hollow body can be formed by a flexible element, for example, as is described above.

For example, in the connected state of the cannula system, the graft material of the hose element can directly abut a (radially) inner surface of the connector, which can be formed, for example, by the above-described base body of the connector. However, it is also possible, for example, for the graft material to abut a flexible element, which can be configured, for example, as a sleeve, as is described above, for example.

If the cannula is the special cannula also proposed here, the cannula, as was already mentioned, can comprise a tension ring, which axially overlaps the front end region of the hose element and is fixedly connected to the front end region of the hose element. Typically, the tension ring is disposed coaxially with respect to the hose element. Typically, the tension ring extends concentrically around the channel in the front end region of the hose element. Typically, a radially inner surface of the tension ring abuts a radially outer surface of the hose element. In principle, however, a reverse configuration is also possible, in which a radially outer surface of the tension ring abuts a radially inner surface of the hose element.

Hereafter, exemplary embodiments are described in which the cannula does not comprise the described tension ring, and exemplary embodiments in which the cannula comprises the tension ring.

In general, two elements, such as the hose element and a reinforcing element or tensioning element, such as the tension ring, are referred to as being fixedly connected here if these cannot be separated from each other without destruction. Such fixed connections can be, for example, integral (such as by adhesive bonding or fusing) or form-locked (such as by sewing). In contrast, two elements are referred to as being detachably connected when these elements can be separated from each other without destruction. For example, pushing the described hollow body into the channel in the front end region of the hose element between the cannula and this hollow body establishes a detachable connection between the cannula and the hollow body, which can be mechanically stabilized, for example, by clamping forces, frictional forces and/or detent forces, as was already described above and will be described in greater detail hereafter.

A basic state of the cannula is defined in that no external forces act on the cannula as a whole, or at least on the front end region of the hose element, and optionally on the tension ring, if present. External forces denote forces that are exerted on the cannula by other bodies, such as the above-described hollow body. The force that the hollow body optionally pushed into the front end region of the hose element may exert on the cannula is an external force within this meaning. In the basic state of the cannula, in particular the described hollow body is thus not pushed into the front end region of the hose element. This hollow body, namely, may exert an (external) force, for example, on the front end region of the hose element and/or on the tension ring, if present, such as a radially outwardly directed force, for example when the inside diameter of the front end region of the hose element in the basic state is smaller than an outside diameter of the front end region of the hollow body.

In the basic state of the cannula, thus exclusively internal forces of the cannula act on the cannula or at least on the front end region of the hose element and, if present, on reinforcing elements or tensioning element, such as the tension ring. Internal forces of the cannula thus shall be understood to mean forces that the different parts of the cannula alternately exert on one another. In the basic state of the cannula, the internal forces mutually compensate one another so that the shape of the cannula does not change over time (or only to a negligibly small degree).

In the basic state of a cannula that does not comprise the described tension ring, the front end region of the hose element, preferably, however, at least the foremost end of the hose element, is typically not preloaded. For example, compared to a hose region axially abutting the front end region, the front end region of the cannula (without the tension ring) thus cannot be expanded, but, in the simplest case, can have the same inside diameter as an abutting hose region.

If, however, the cannula comprises the described tension ring, the front end region of the hose element, and preferably at least the foremost end of the hose element, is preloaded in the basic state of this cannula by an (internal) force that is exerted by the tension ring onto the front end region of the hose element and directed radially outwardly. Preferably, the tension ring exerts the described radial force onto at least the foremost end of the hose element. In the basic state of the cannula, provided the cannula comprises the described tension ring, the cannula is thus, in particular, also preloaded as described when the described hollow body has not been pushed into the front end region of the hose element.

This preloading by the tension ring, if present, allows the shape of the hose element to be stabilized in the front end region, and preferably at least at the foremost end of the hose element. In this way, the establishment of a connection to a hollow body can be simplified, in particular when the hose element is made of a soft and/or flexible material in the front end region.

In particular, the front end region of the hose element, and preferably at least the foremost end of the hose element, can be elastically expanded by the tension ring, if present. As a result of the expansion, a larger diameter of the front inlet opening of the channel at the foremost end of the hose element can be achieved. The front opening can be radially circumscribed, for example, by the foremost end of the hose element itself or, if present, by the tension ring (to the extent this is disposed in the channel, as has been described above). Due to the enlarged front opening, the establishment of a connection to the described hollow body can be simplified. For example, the front opening can be found more easily during insertion of the hollow body into the channel. Moreover, as a result of the expansion, the axial insertion of the hollow body into the channel can be carried out in a more controlled manner and using a smaller axial force.

For example, it is possible that, in the basic state of the cannula, an inside diameter of the hose element within the front end region increases toward the front opening of the channel. For example, in the basic state of the cannula, the inside diameter of the hose element can increase within the front end region toward the tension ring, if present.

The described inside diameter can be, for example, a respective smallest inside diameter or an averaged inside diameter of the hose element.

Typically, the tension ring, if present, does not protrude axially beyond the front end region of the hose element. In particular, the tension ring, if present, typically does not protrude axially toward the front beyond a foremost end of the hose element, but ends at or even behind this. Typically, the tension ring, if present, extends circumferentially and/or concentrically around the channel in the front end region of the hose element. In one exemplary embodiment, a radially inner surface of the tension, if present, abuts a radially outer surface of the hose element. In this example, the tension ring is thus disposed outside the channel. In another exemplary embodiment, a radially outer surface of the tension ring, if present, abuts a radially inner surface of the hose element. In this example, the tension ring is thus (at least partially) disposed inside the channel.

Due to the fixed connection to the hose element and the arrangement in the front end region of the hose element, the tension ring, if present, in particular also enables a transmission of external forces, and in particular of axial tensile forces or axial pushing forces, onto the hose element. Typically, such external forces are exerted on the hose element during the establishment of the connection to the hollow body, that is, in particular, when the hose element is being pushed onto the hollow body or the hollow body is pushed into the hose element. In this way, the tension ring, if present, can also perform the function of a force transmission element, and in particular of a pulling element. For this purpose, the tension ring, if present, can optionally include a radial widening which, for example, radially protrudes beyond a radially outer surface of the hose element, so as to enable, by way of this widening, the transmission of the above-described forces onto the tension ring and, via the tension ring, onto the hose element.

In one exemplary embodiment, the cannula comprises a sealing ring. Typically, the sealing ring is disposed coaxially with respect to the hose element, and moreover coaxially with respect to the tension ring. Typically, the sealing ring extends circumferentially and/or concentrically around the channel in the front end region of the hose element. Typically, a radially inner surface of the sealing ring abuts a radially outer surface of the hose element.

The sealing ring is positioned, for example, so as to axially overlap the front end region of the hose element and, for example, so as to be disposed axially behind the tension ring, if present. The sealing ring is typically axially spaced apart from the tension ring, if present. For example, a rear end of the sealing ring can protrude axially toward the rear beyond a rear end of the front end region of the hose element. However, it is also possible for an axial position of the rear end of the sealing ring to coincide with an axial position of the rear end of the front end region of the hose element. If the cannula comprises the described sealing ring, no external forces act on the sealing ring in the above-defined basic state of the cannula. In the basic state, for example, an inside diameter of the hose element on the tension ring may be greater than an inside diameter of the hose element at the sealing ring. The described inside diameters can each be smallest inside diameters, for example. Typically, the hose element has an approximately identical wall thickness at the sealing ring and at the tension ring.

In the basic state of the cannula, an inside diameter of the sealing ring can increase toward the front, that is, toward the foremost end of the hose element. In other words, the sealing ring can taper toward the rear end region of the hose element, in the basic state of the cannula. In this way, the hollow body is guided in the radial direction during the axial insertion into the channel of the hose element, and centering of the hollow body is improved. For example, the inner surface of the sealing ring can have a conical shape.

The sealing ring can be displaceable and/or rotatable relative to the hose element, for example. This enables an easier assembly of the cannula. In many cases, however, this can also simplify the insertion of the hollow body into the channel of the hose element. For example, during insertion of the hollow body, the hose element (for example, due to frictional forces between the hose element and the hollow body) can shift axially toward the rear relative to the sealing ring, whereby, for example, creases of the hose element in the front end region can be removed or decreased, so that the hose element, in the front end region, and in particular at the sealing ring, rests against the hollow body substantially without creasing. In this way, enhanced sealing is achieved, and the risk of the formation of thrombi is reduced.

For example, the tension ring, if present, can be integrally joined to the hose element, for example by adhesively bonding or fusing the tension ring to the hose element. As an alternative or in addition, the tension ring can be sewn to the hose element. The tension ring can include holes, for example, through which a sewing thread connecting the tension ring to the hose element extends.

The tension ring, if present, is typically designed to be more rigid than the hose element, and also more rigid than the sealing ring (if present). For example, the tension ring can be made of a stronger material than the hose element, and can also be made of a stronger material than the sealing ring (if present). Typically, the tension ring and the sealing ring (if present) are each made of a stronger material than the hose element. For example, the tension ring, the sealing ring, and the further sealing ring can be made of biocompatible or hemocompatible materials, for example of appropriate polymers, and in particular of silicone.

Typically, the hose element can, for example, be made of a biocompatible or hemocompatible material, for example of a graft material. For example, the hose element can thus comprise a textile carrier structure, which can have a tubular design, for example. The textile carrier structure can be made of a polyester woven fabric and/or be sealed with a coating, for example.

The cannula can further include an operating element, which typically comprises a sleeve-shaped base body. The sleeve-shaped base body can have an outer grip surface, for example. Moreover, the sleeve-shaped base body can define an interior region in which the front end region of the hose element, the tension ring, if present, and preferably also the sealing ring, if present, are disposed. Typically, the sleeve-shaped base body includes one or more receiving regions on an inner surface defining the interior space. For example, the receiving region can be provided for the tension ring, if present and, optionally, also includes a receiving region for the sealing ring. Such receiving regions can be defined, for example, by annular grooves or by radially inwardly protruding indentations of the sleeve-shaped base body.

For example, a fixed connection between the sealing ring, if present, and the sleeve-shaped base body can be dispensed with. For example, the sealing ring can exclusively be joined to the sleeve-shaped base body in a form-locked and/or force-fit manner. The same can also apply to the connection of the tension ring, if present, and of the hose element to the sleeve-shaped base body.

The operating element can be used to handle the cannula manually. Preferably, the described connection of the cannula to the hollow body can be established by a (purely) manual operation of the operating element. For this purpose, in particular external forces, and in particular axial tensile forces or axial pushing forces, can be transmitted via the operating element onto the hose element. This force transmission onto the hose element can be carried out, for example, via the tension ring, if present, as has been described above. For this purpose, it may be provided, for example, that the tension ring is supported in the axial direction relative to the sleeve-shaped basic body by one of the above-described receiving regions of the sleeve-shaped basic body, and in particular by an annular groove or a radially inwardly protruding indentation. In the case of the radially inwardly protruding indentation, for example, this is typically disposed axially behind the tension ring, or axially behind the above-described optional radial widening of the tension ring, so that the described axial tensile forces or axial pushing forces can be transmitted forwardly onto the tension ring by means of this indentation.

Moreover, the operating element can comprise one or more flexible detent arms (spring arms), which typically protrude axially from a front end of the sleeve-shaped base body in a cantilevered manner beyond the front end region of the hose element. Each of the detent arms can comprise a radially inwardly directed detent tooth, for example, which can be configured to form a detent connection with a respective corresponding mating detent element. The respective mating detent element can be disposed, for example, on an outer surface of the hollow body that is provided for a connection to the cannula, as is described in greater detail hereafter.

The cannula system proposed here comprises a cannula of the type proposed here and the described hollow body, which is provided for a connection to the cannula. The hollow body can be configured as a tube, for example, and in particular as a pump inlet or as a pump outlet of a blood pump. The hollow body likewise defines a channel for conducting a liquid, such as blood. Typically, the hollow body is made of a biocompatible or hemocompatible material. For example, the hollow body is made entirely or at least in some regions of a metallic material, such as a stainless steel or a titanium alloy, or is made entirely or in some regions of a polymer, such as a silicone. As described above, combinations of different materials are also possible. For example, the hollow body can comprise a reinforcing sleeve that is made of a metallic material and embedded into a polymer (such as silicone), and in particular, the front end region of the hollow body can be configured in this way.

Typically, the hollow body has a higher strength than the hose element, which can typically be made of a very soft, compliant material and additionally can be designed to be more thin-walled than the hollow body.

The hollow body comprises a front end region. The front end region of the hollow body is shaped so as to be pushable through the front opening of the channel of the hose element into the channel of the hose element, so that the front end region of the hollow body axially overlaps the front end region of the hose element. Typically, the front end region of the hose element and the front end region of the hollow body have an axial extension equal in size. In the pushed-in state, the channels of the hose element and of the hollow body form a continuous channel.

The hollow body can comprise a stop up to which the hollow body can be pushed into the channel. The stop itself thus does not form part of the front end region of the hollow body, but is disposed axially behind the front end region of the hollow body. The stop defines a maximum axial depth to which the hollow body can be pushed into the channel. The stop can be configured, for example, in the form of a radial widening of the hollow body, for example in the form of a ridge on an outer surface of the hollow body.

As was already mentioned above, the hollow body can comprise at least one detent element or a mating detent element for establishing a detent connection between the cannula and the tube. The at least one detent element or mating detent element can be formed, for example, by a surface region of the above-described stop.

In the basic state of the cannula, a diameter, for example a smallest diameter, of the front opening of the channel, which is typically formed by the foremost edge of the front end region of the hose element, is preferably greater than an outside diameter of the hollow body at a foremost end of the front end region of the hollow body. In addition, or as an alternative, in the basic state of the cannula, the diameter of the front end region of the channel of the hose element, for example the smallest diameter, can be greater than a largest outside diameter of the front end region of the hollow body, wherein the front end region can be defined, for example, by the above-described stop, as described above. However, it may also be provided, for example, that, in the basic state of the cannula, the diameter of the front opening of the channel of the hose element, for example the smallest diameter, is (slightly) smaller than a largest outside diameter of the front end region of the hollow body, wherein the front end region can be defined, for example, by the above-described stop. In this case, the front end region of the hose element is slightly radially expanded by the front end region of the hollow body at least in some regions when the front end region of the hollow body is inserted into the front end region of the hose element.

For example, when the front end region, for example to the extent that the described stop allows, is pushed into the channel, a clear gap may exist between the hose element and the hollow body, which extends around the hollow body in an annular manner (annular gap), for example. The gap is typically disposed within the channel of the hose element and in an axial overlapping region of the tensioning element and of the hose element.

If the above-described sealing ring is provided, this is preferably disposed so as to axially overlap the end region of the hollow body that is pushed into the channel (if necessary, up to the stop). In an axial overlapping region, in which the front end region of the hollow body that is pushed in (if necessary, up to the stop) and the sealing ring axially overlap, a mutual (radial) pressing force exists between the hose element and the hollow body, which is caused by the sealing ring, whereby sealing is effectuated between the hollow body and the hose element. The intensity of this mutual pressing force can be adapted, for example, by a suitable selection of the inside diameter of the sealing ring and/or of the strength of the sealing ring. The sealing ring is typically elastically expanded by the inserted hollow body. If such a sealing ring is not provided, a mutual pressing force between the hose element and the inserted hollow body can also be effectuated, for example, by the elasticity of the hose element (which is radially expanded by the hollow body). Typically, no radial elongation of the hose element by the inserted hollow body (but only by the tension ring) takes place in the axial overlapping region with the tension ring, if present. Typically, a radial elongation of the hose element by the inserted hollow body takes place, if at all, only axially behind the tension ring.

The front end region of the hollow body pushed into the channel (up to the stop) can end, for example, within or at a rear end of the above-described axial overlapping region of the hose element and of the sealing ring. In this way, liquid can be prevented from flowing between the hose element and the hollow body (pocket formation).

The blood pump system of the type proposed here comprises one of the cannula systems proposed here (for example, in an embodiment without a tension ring, but with a connector, or in an embodiment with a tension ring and without a connector) and a blood pump, typically an implantable blood pump. The cannula is then typically configured as an implantable vascular prosthesis. For example, the hose element is made of a graft material in this case and, for example, comprises a textile carrier structure, as was already described.

The blood pump typically comprises a pump housing. The pump housing comprises a pump inlet and a pump outlet, which typically have a tubular configuration. For example, the hollow body of the cannula system forms the pump outlet or the pump outlet of the blood pump. Further optional features of the blood pump will be described hereafter in connection with specific exemplary embodiments.

The following aspects relate to exemplary embodiments of a cannula, of a cannula system and of a blood pump system, in which the cannula comprises the described tension ring. FIGS. 1 to 10 show such exemplary embodiments. The reference numerals indicated in the aspects relate to these figures.

1. A cannula (7) for conducting a liquid, in particular blood, comprising:
   a hose element (9) including a front end region (11) and a rear end region, wherein a channel (10) extends from the front end region (11) of the hose element (9) to the rear end region the of hose element (9) through the hose element (9);
   a tension ring (19), wherein the tension ring (19) axially overlaps the front end region (11) of the hose element (9) and is fixedly connected to the front end region (11) of the hose element (9),
   wherein, in the basic state of the cannula (7) in which no external forces act on the front end region (11) of the hose element (9) and on the tension ring (19), the hose element (9) is preloaded by a radially outwardly directed force exerted by the tension ring (19) onto the front end region (11) of the hose element (9).

2. The cannula (7) according to aspect 1, characterized in that the hose element (9) is elastically expanded by the tension ring (19) in the front end region (11) of the hose element (9).

3. The cannula (7) according to any one of the preceding aspects, characterized in that, in the basic state of the cannula (7), an inside diameter of the hose element (9) increases within the front end region (11) toward the tension ring (19).

4. The cannula (7) according to any one of the preceding aspects, characterized in that the cannula (7) comprises a sealing ring (28), the sealing ring (28) axially overlapping the front end region (11) of the hose element (9) and being disposed axially behind the tension ring (19).

5. The cannula (7) according to aspect 4, characterized in that the sealing ring (28) is axially spaced apart from the tension ring (19).

6. The cannula (7) according to one of aspects 4 or 5, characterized in that, in the basic state of the cannula (7) in which additionally no external forces act on the sealing ring (28), an inside diameter of the hose element (9) at the tension ring (19) is greater than an inside diameter of the hose element (9) at the sealing ring (28).

7. The cannula (7) according to any one of aspects 4 to 6, characterized in that the tension ring (19) is designed to be more rigid than the sealing ring (28) and/or that the tension ring (19) is made of a stronger material than the sealing ring (28).

8. The cannula (7) according to any one of aspects 4 to 7, characterized in that, in the basic state of the cannula (7), the sealing ring (28) tapers toward the rear end region of the hose element (9), a radially inner surface (31) of the sealing ring (28) preferably having a conical shape.

9. The cannula (7) according to any one of aspects 4 to 8, characterized in that the sealing ring (28) is displaceable and/or rotatable relative to the hose element (9).

10. The cannula (7) according to any one of the preceding aspects, characterized in that the tension ring (19) is integrally joined to the hose element (9) or sewn to the hose element (9).

11. The cannula (7) according to any one of the preceding aspects, characterized in that the hose element (9) is made of a graft material and/or comprises a textile carrier structure.

12. The cannula (7) according to any one of the preceding aspects, characterized in that the cannula (7) comprises an operating element (34) having a sleeve-shaped base body (35), the sleeve-shaped base body (35) defining an interior region (37), wherein the front end region (11) of the hose element (9), the tension ring (19) and, to the extent that this aspect refers back to one of aspects 4 to 9, preferably also the sealing ring (28), are disposed in the interior region (37) of the sleeve-shaped base body (35).

13. The cannula (7) according to aspect 12, characterized in that the operating element (34) comprises at least one detent element (40), for example at least one detent arm.

14. A cannula system (2), comprising a cannula (7) according to any one of the preceding aspects and a hollow body (8), in particular a tube, wherein the hollow body (8) includes a front end region (15), which can be inserted into the channel (10) of the hose element (9) through a front inlet opening (14) of the channel, in the basic state of the cannula (7), in which the front end region (15) of the hollow body (8) is not pushed into the channel (10) of the hose element (9), a diameter of the front inlet opening (14) of the channel (10) being greater than an outside diameter of the front end region (15) of the hollow body (8).

15. A blood pump system (1) comprising a blood pump (3) and a cannula system (2) according to aspect 14, characterized in that the blood pump (3) comprises a pump housing (4) having a pump inlet (5) and a pump outlet (6), the hollow body (8) of the cannula system forming the pump outlet (5) or the pump inlet (6) of the blood pump (3).

Figure 2:
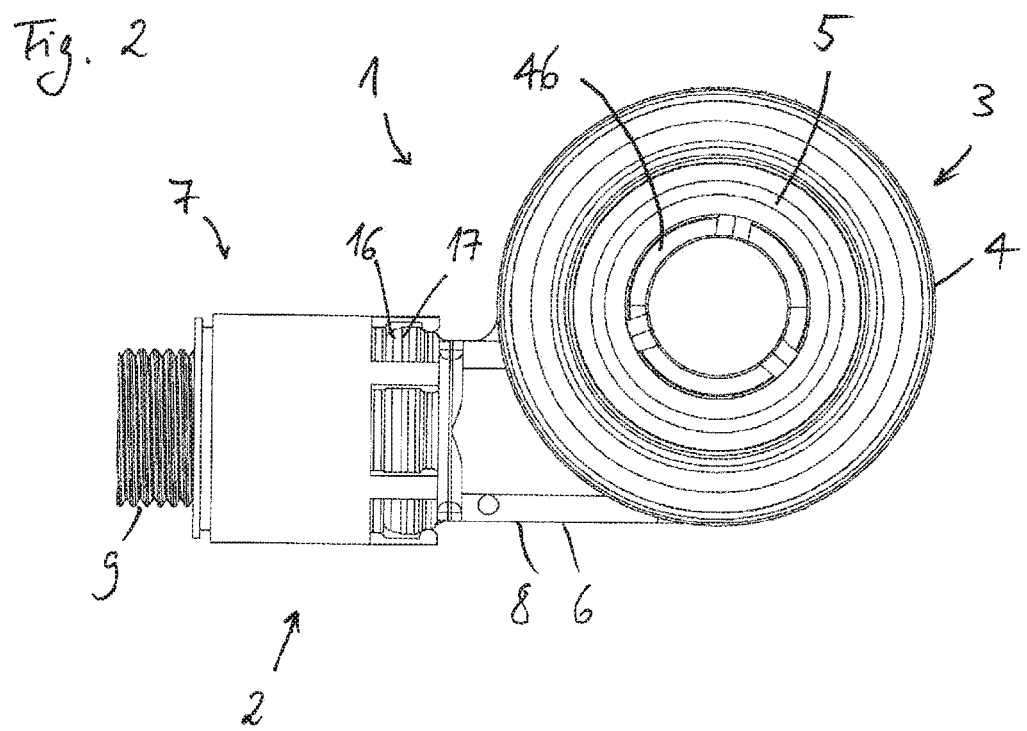
FIG. 2 shows the blood pump system shown in FIG. 1 in a view from above.
Figure 3:
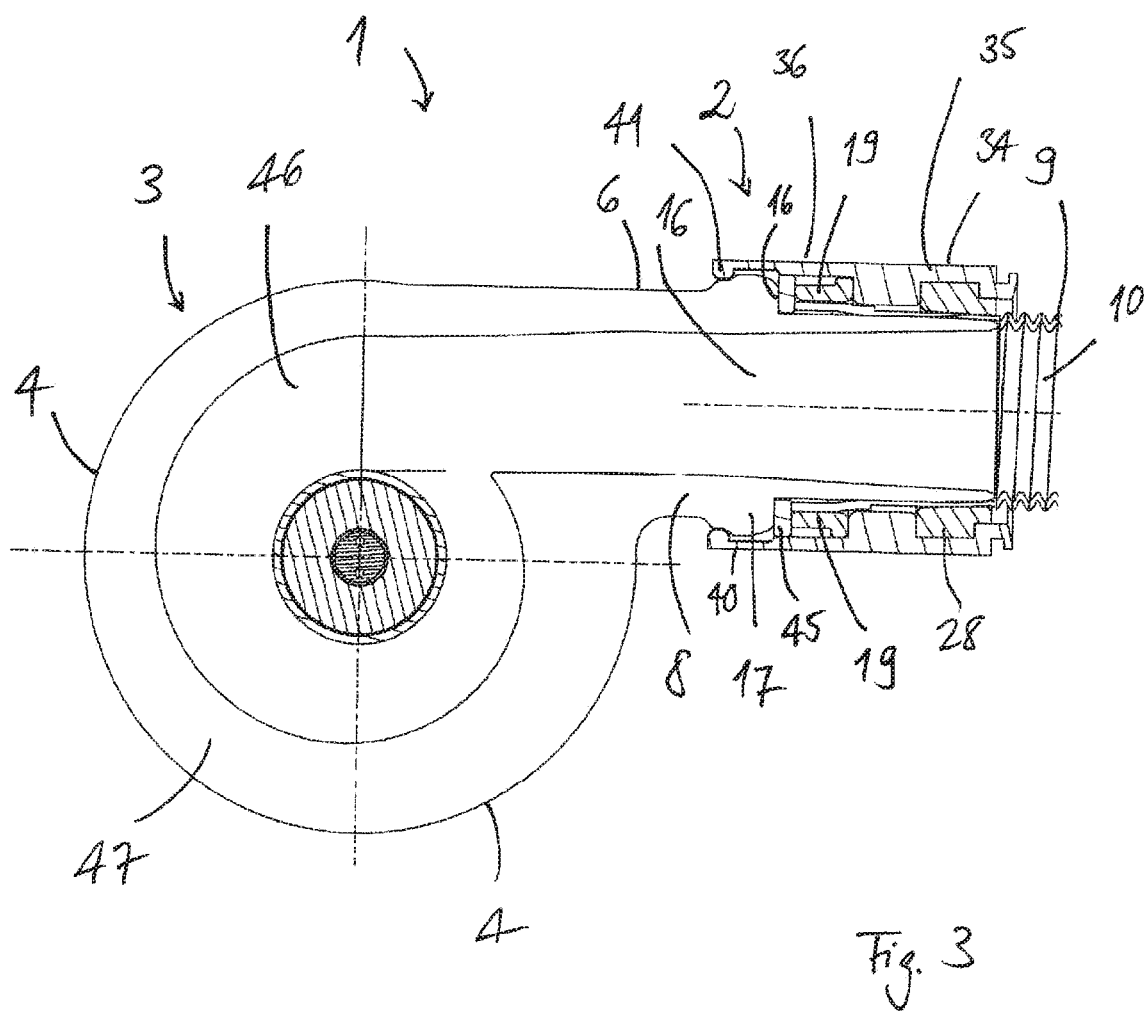
FIG. 3 shows the blood pump system shown in FIG. 1 in a sectional illustration.
Figure 4A:
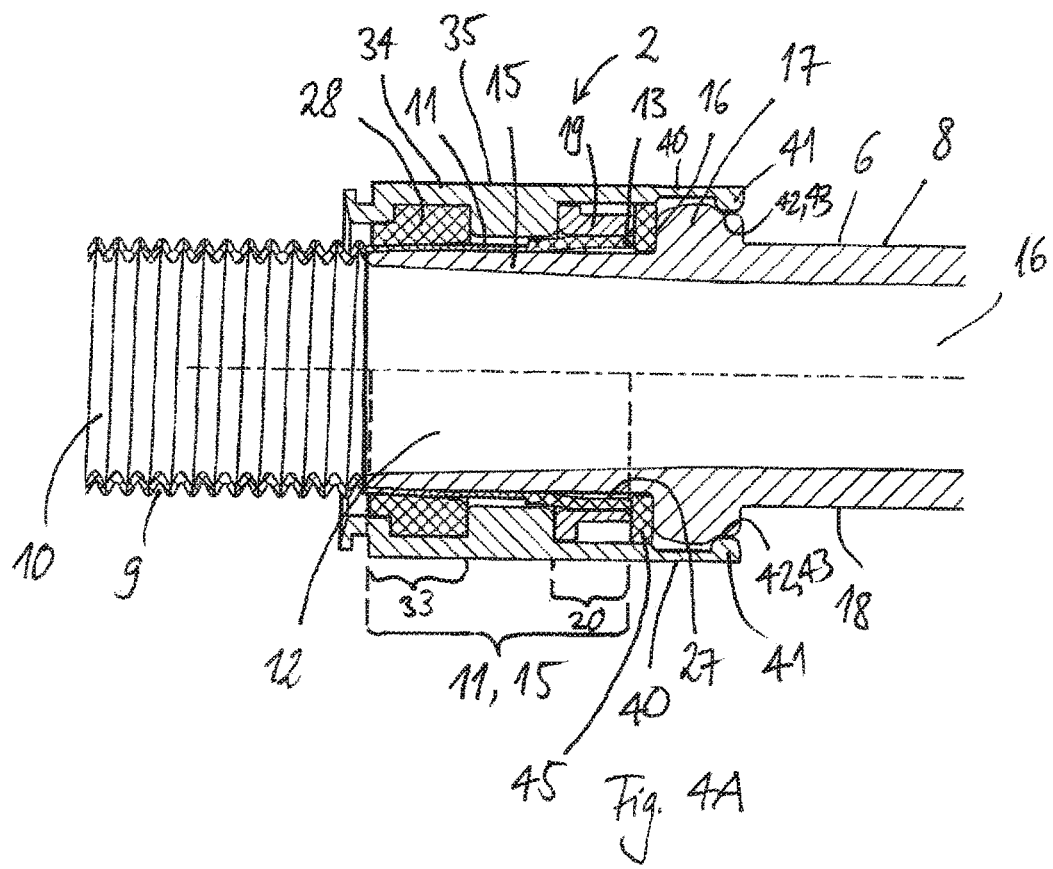
FIG. 4A shows a cannula system of the blood pump system shown in FIG. 1 in a longitudinal sectional illustration.
Figure 4B:
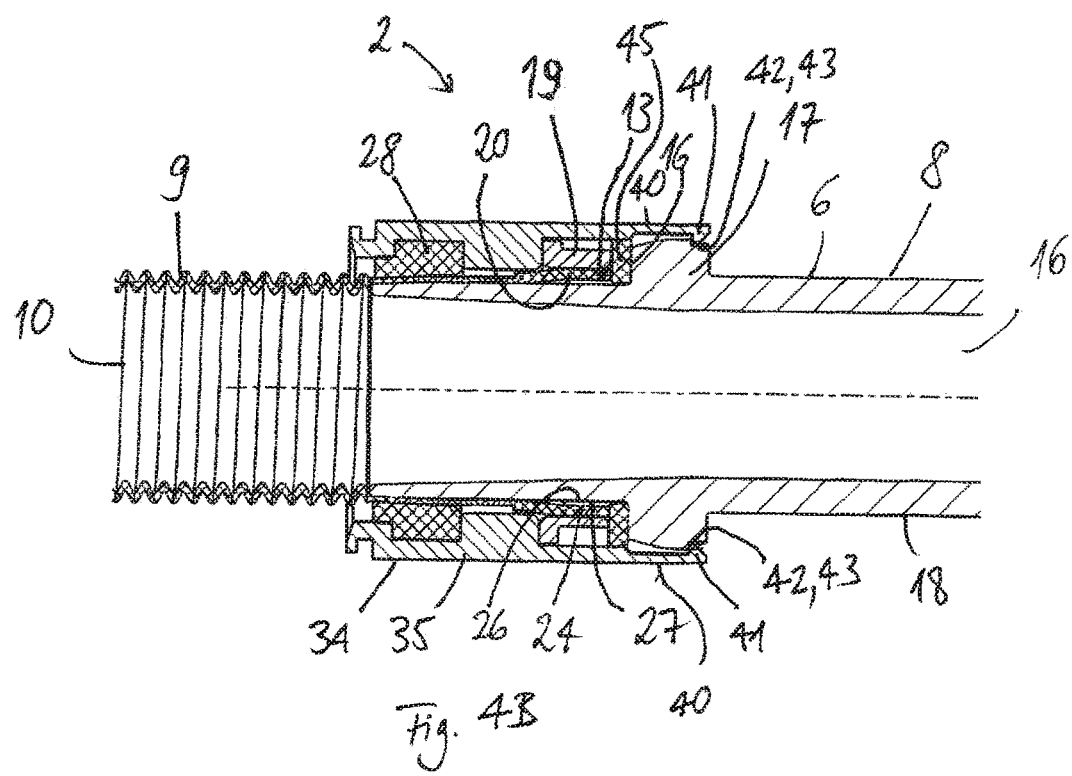
FIG. 4B shows a variant of the cannula system shown in FIG. 4A in a longitudinal sectional illustration in a connected state.
Figure 5A:
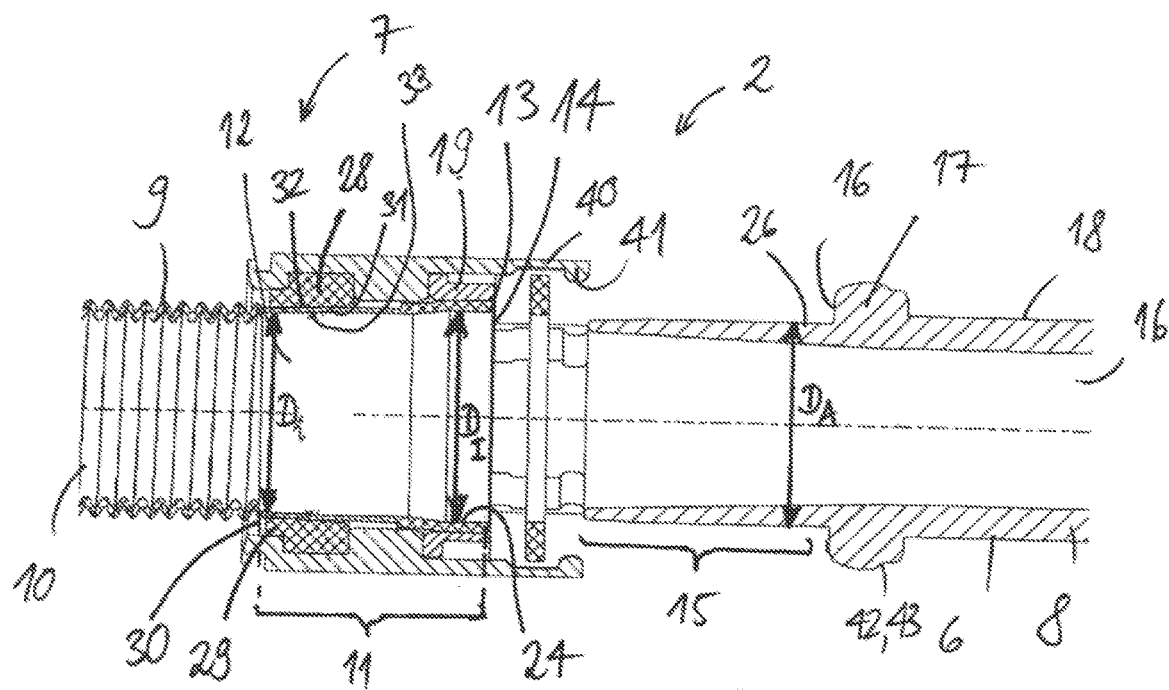
FIGS. 5A, 5B shows a side view and a perspective view of a longitudinal section through the cannula system shown in FIG. 4A in a separated state.
Figure 5B:
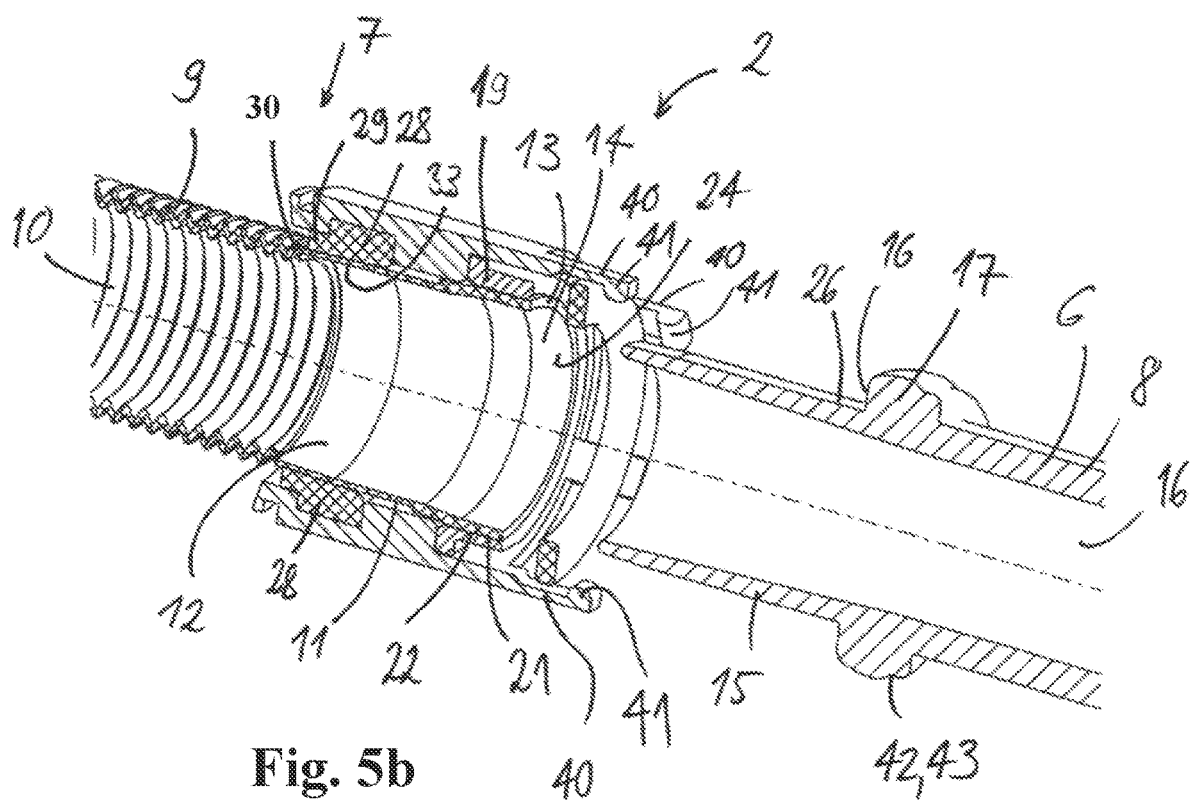
Figure 6A:
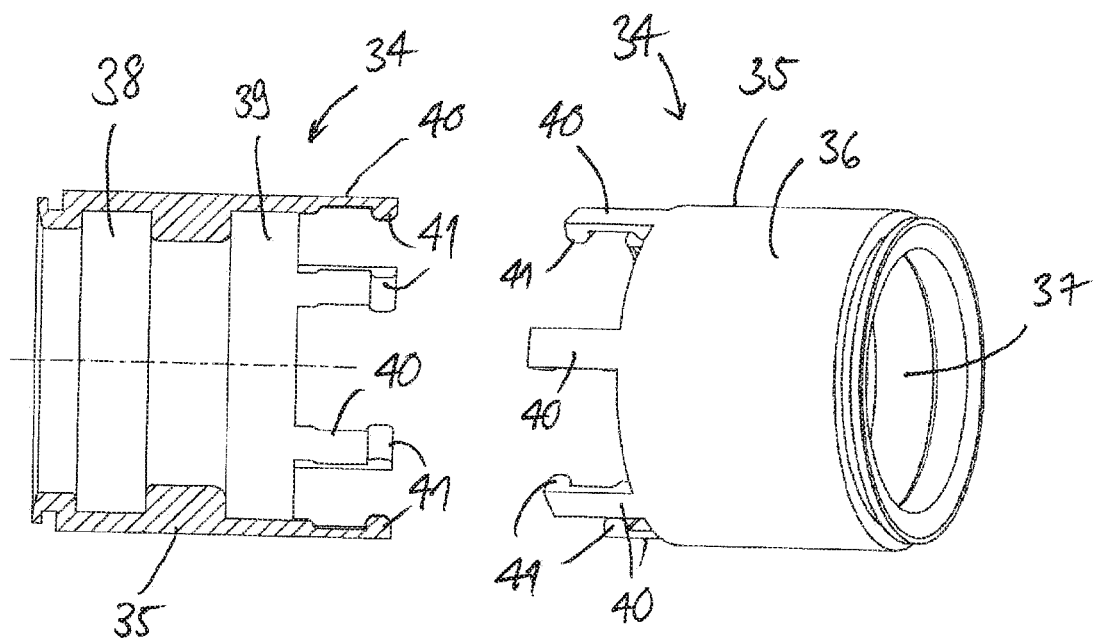
FIG. 6A shows an operating element of a cannula of the cannula system shown in FIG. 4A in a sectional illustration and in a perspective illustration.
Figure 6B:
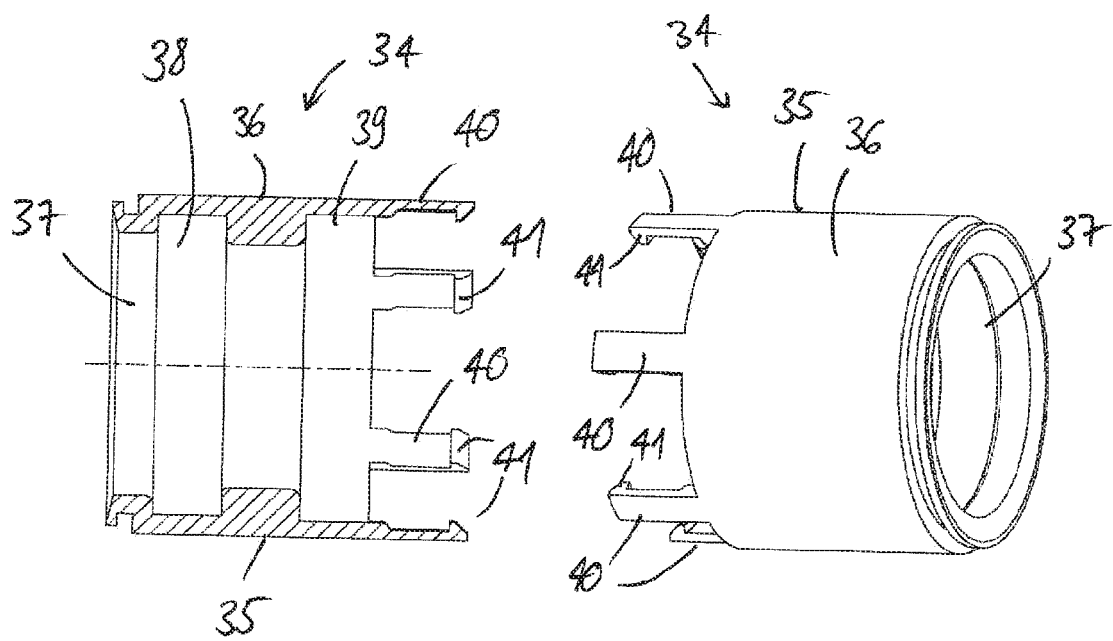
FIG. 6B shows an operating element of a cannula of the cannula system shown in FIG. 4B in a sectional illustration and in a perspective illustration.
Figure 8:
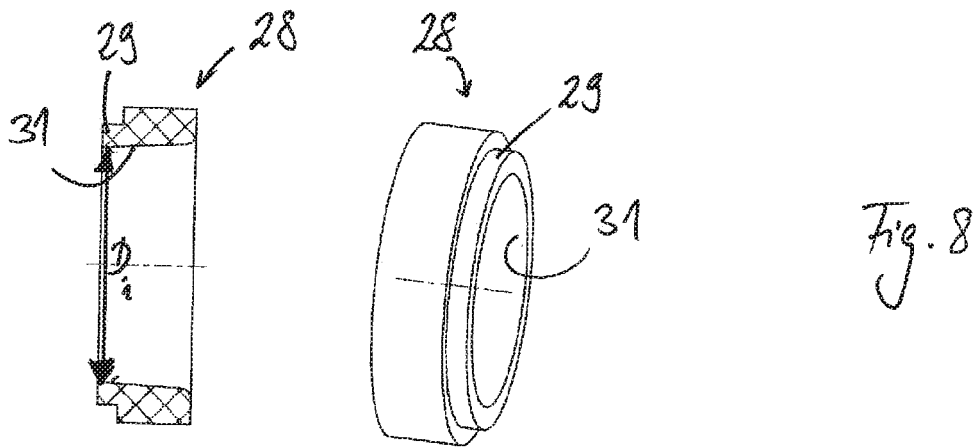
FIG. 8 shows a sealing ring of the cannula system shown in FIG. 4A or in FIG. 4B in a longitudinal sectional illustration and in a perspective illustration.
Figure 9:
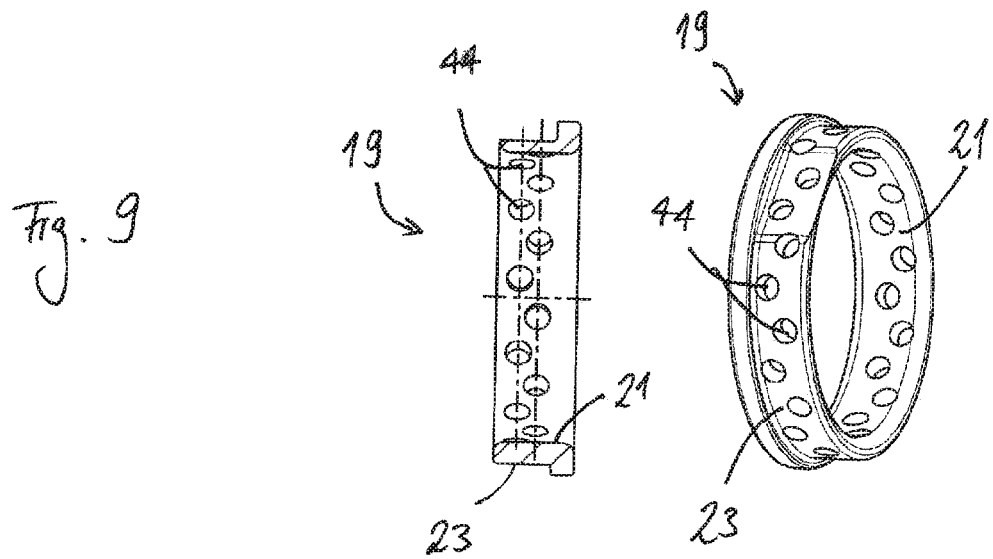
FIG. 9 shows a tension ring of the cannula system shown in FIG. 4A or in FIG. 4B in a longitudinal sectional illustration and in a perspective illustration.
Figure 10:
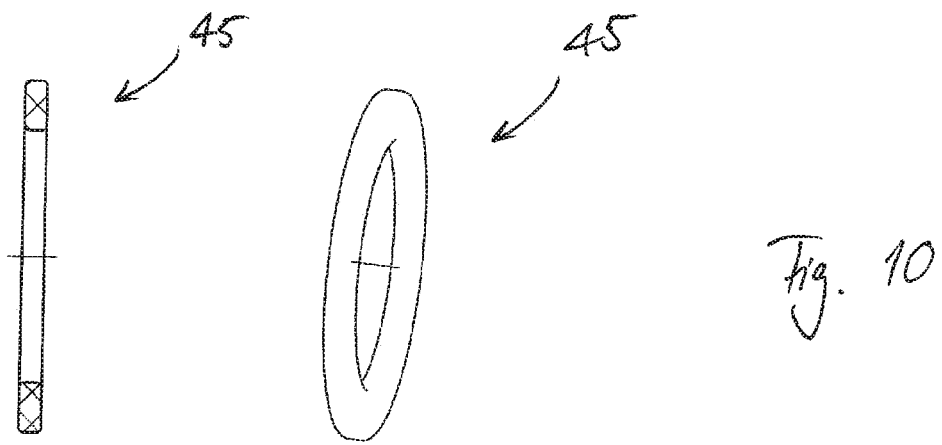
FIG. 10 shows a further sealing ring of the cannula system shown in FIG. 4A or in FIG. 4B in a longitudinal sectional illustration and in a perspective illustration.
Figure 13:
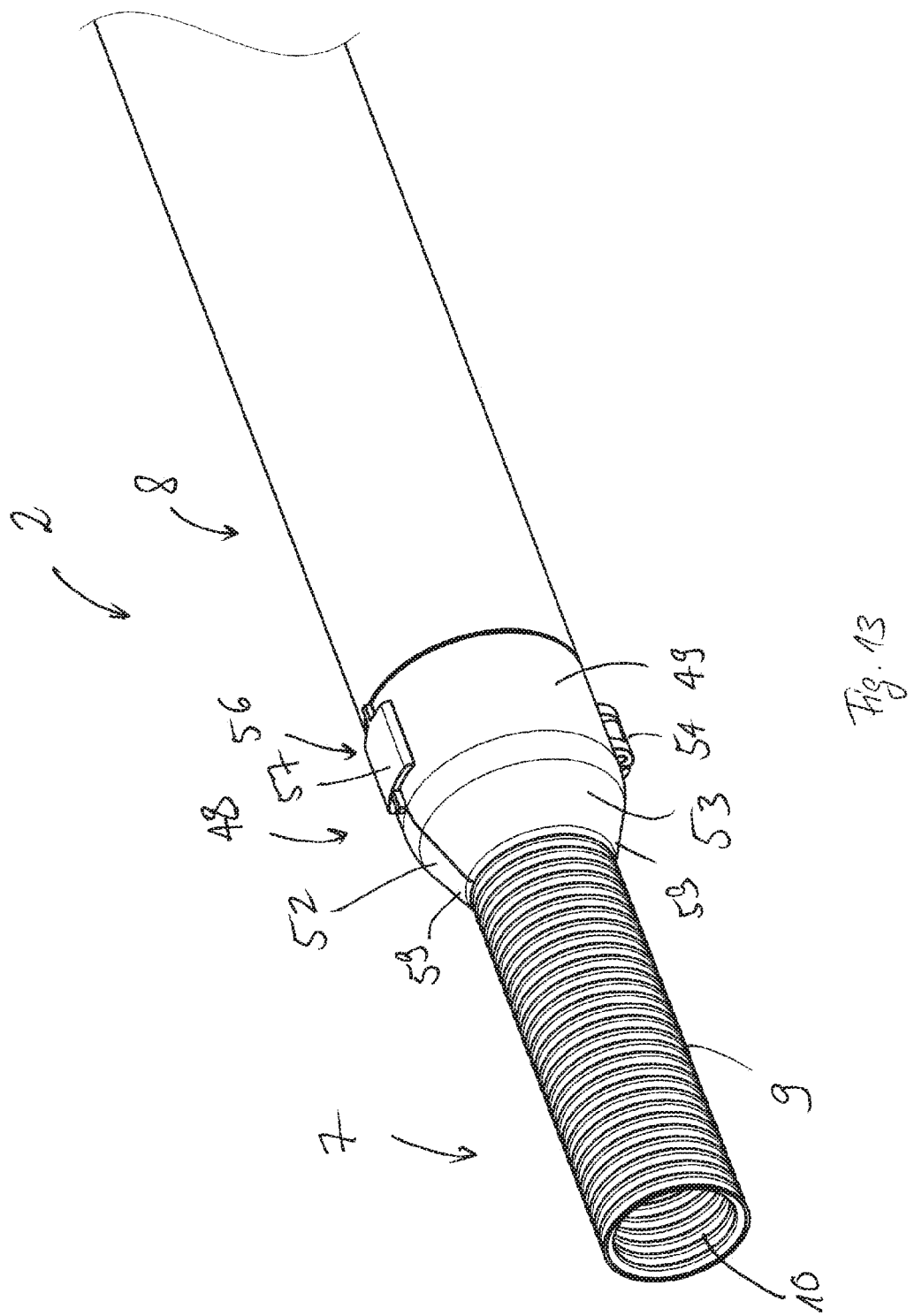
FIG. 13 shows a perspective illustration of the cannula shown in FIG. 11 and of the hollow body, which are connected by means of a connector of the cannula system.
Figure 14:
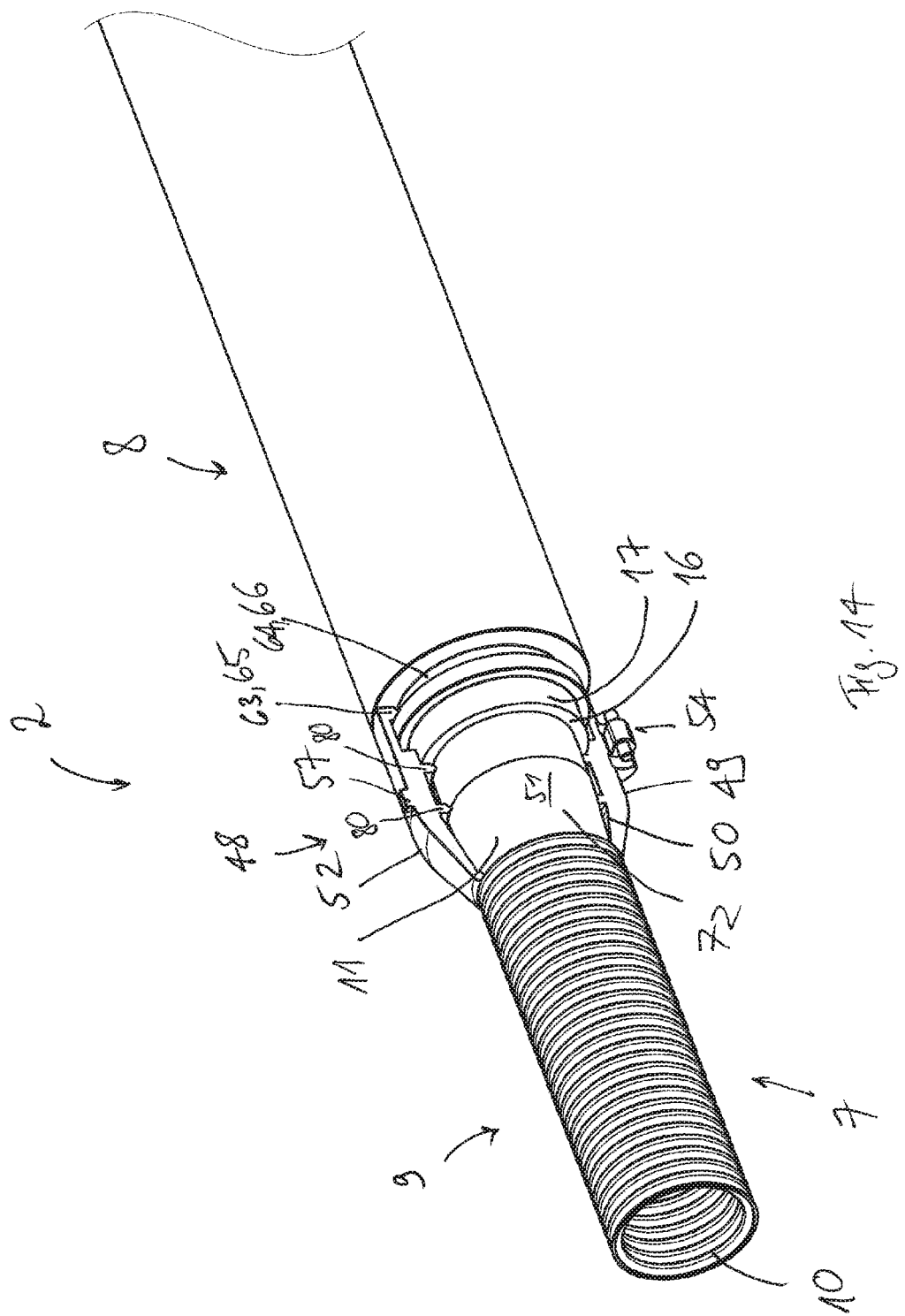
FIG. 14 shows a perspective illustration of the cannula system of FIG. 13, wherein however one of two half shells of the connector is not shown.
Figure 15:
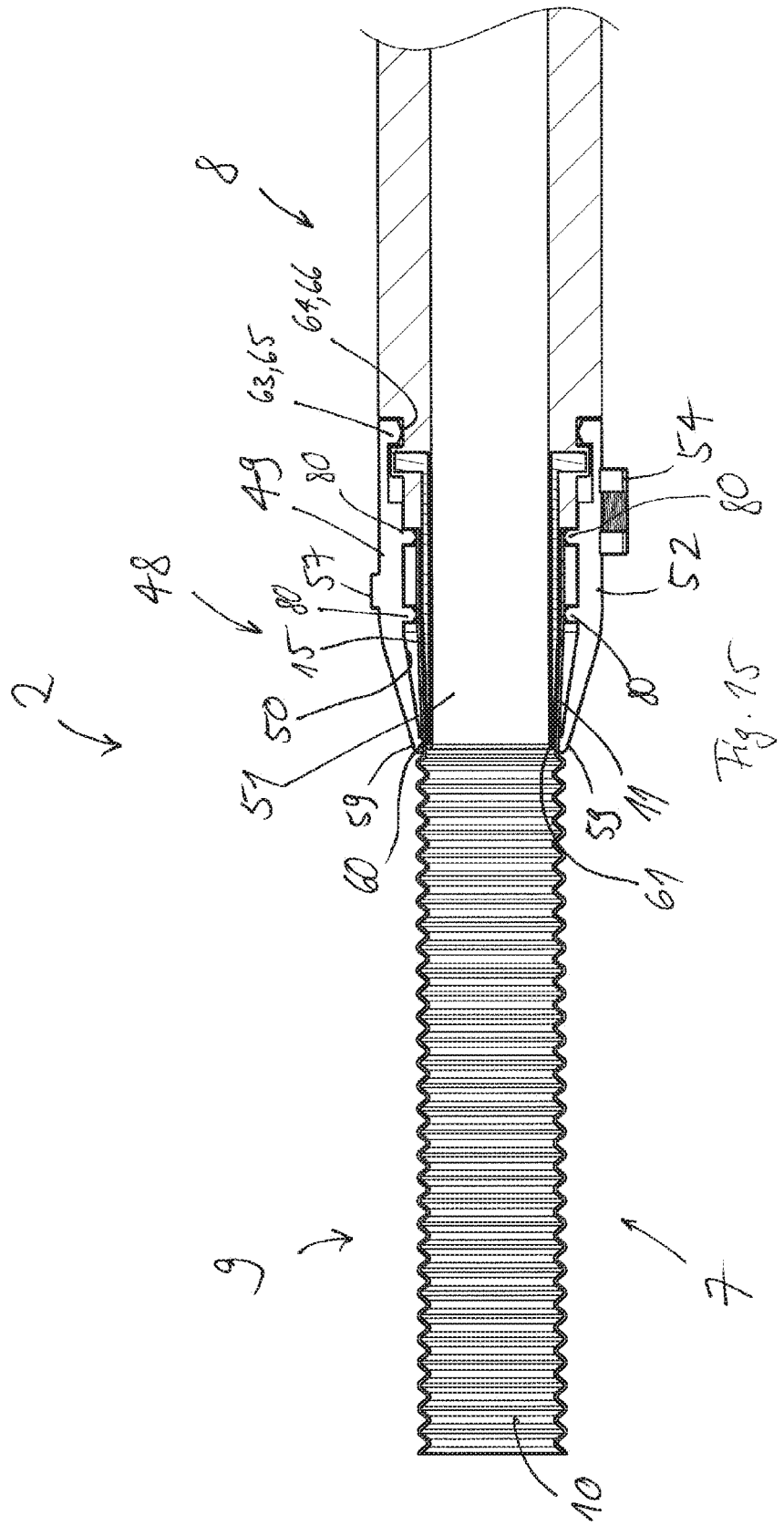
FIG. 15 shows a longitudinal section through the cannula system of FIG. 13.
Figure 16:
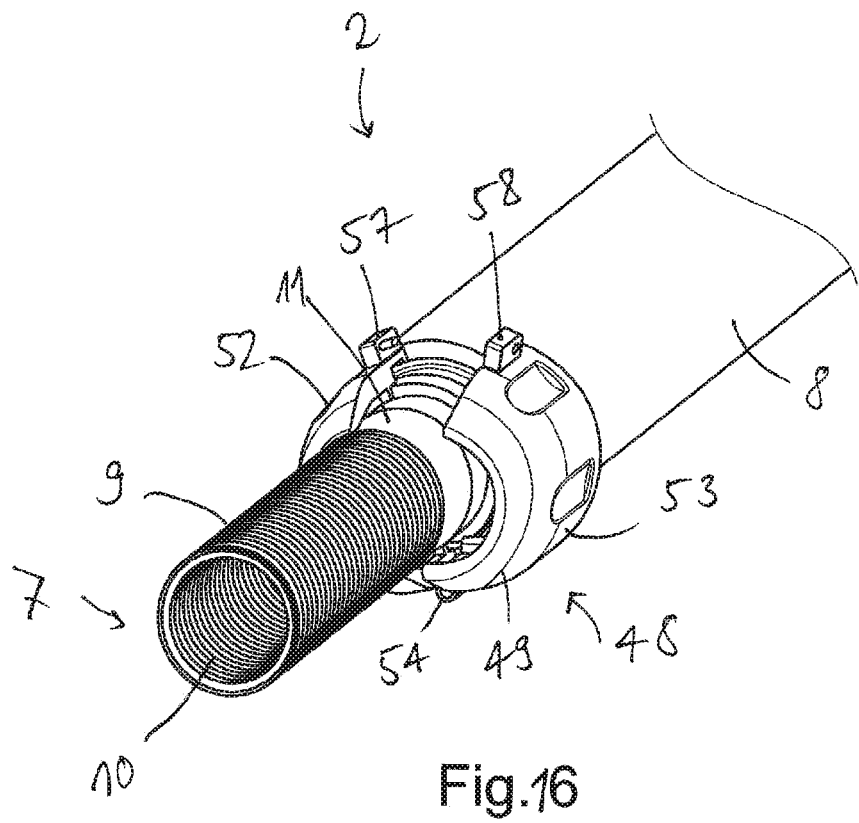
FIG. 16 shows a perspective illustration of the cannula system of FIG. 13, wherein the two half shells of the connector are pivoted apart.
Figure 17:
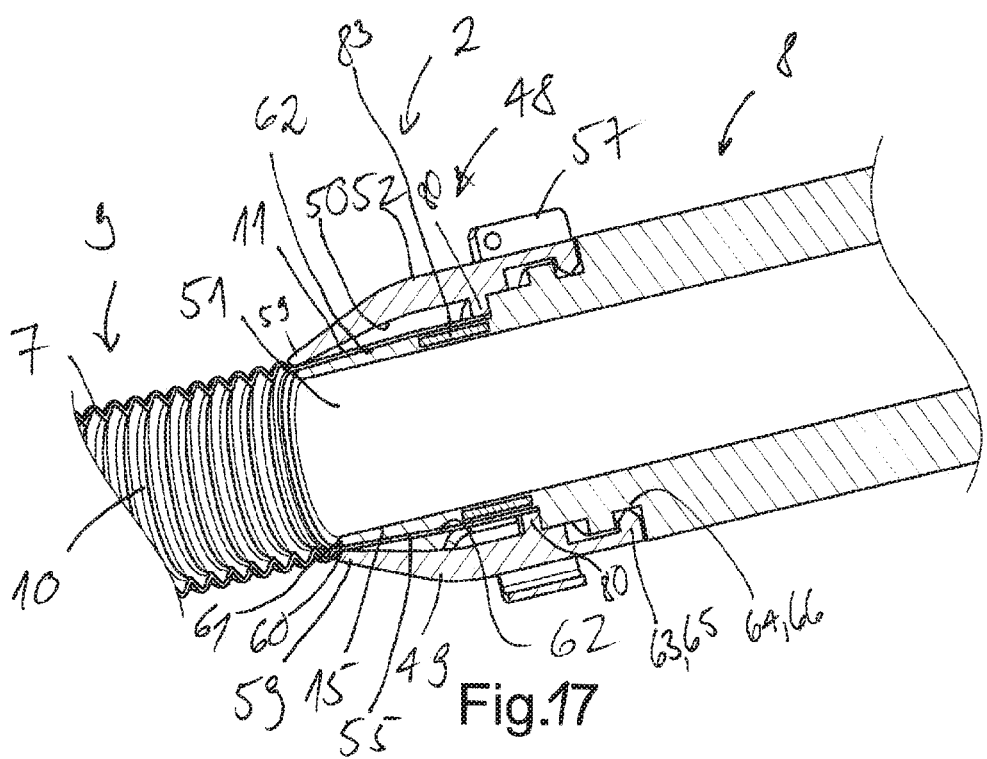
FIG. 17 shows a longitudinal section through a modification of the cannula system of FIG. 13.
Figure 20:
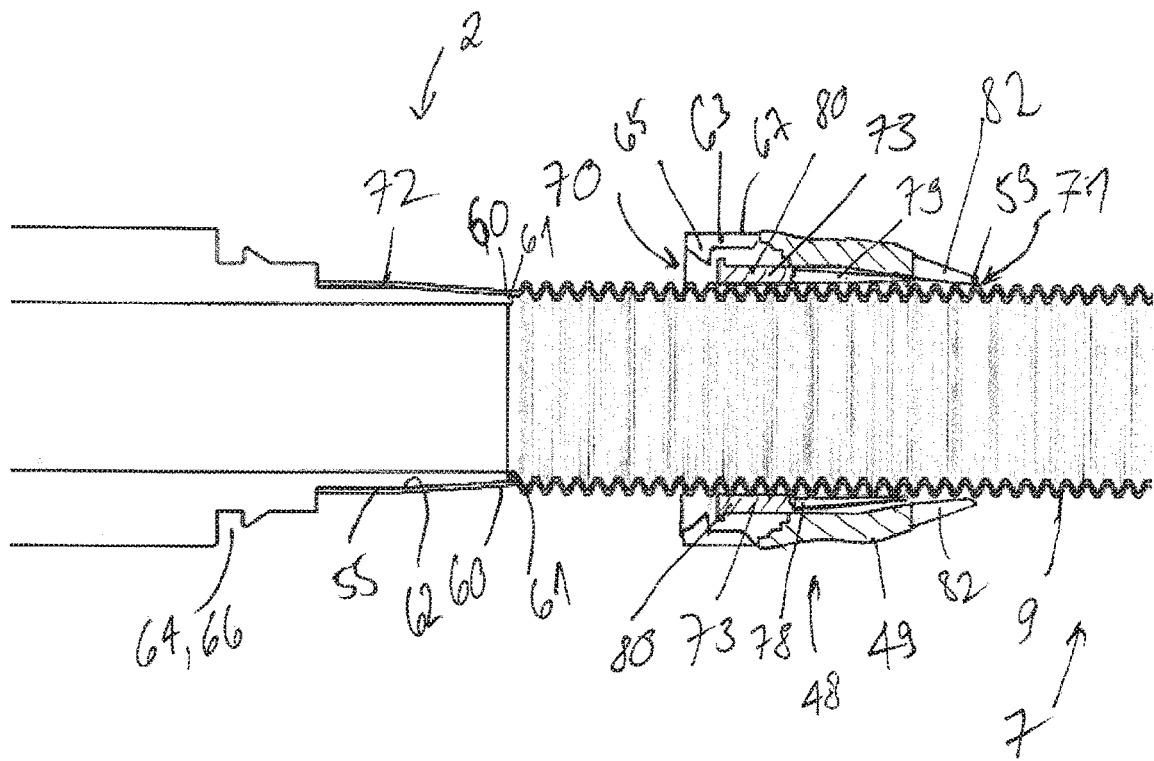
FIGS. 20, 21 show a longitudinal section through the cannula system shown in FIG. 18 with different axial positions of the connector.
Figure 21:
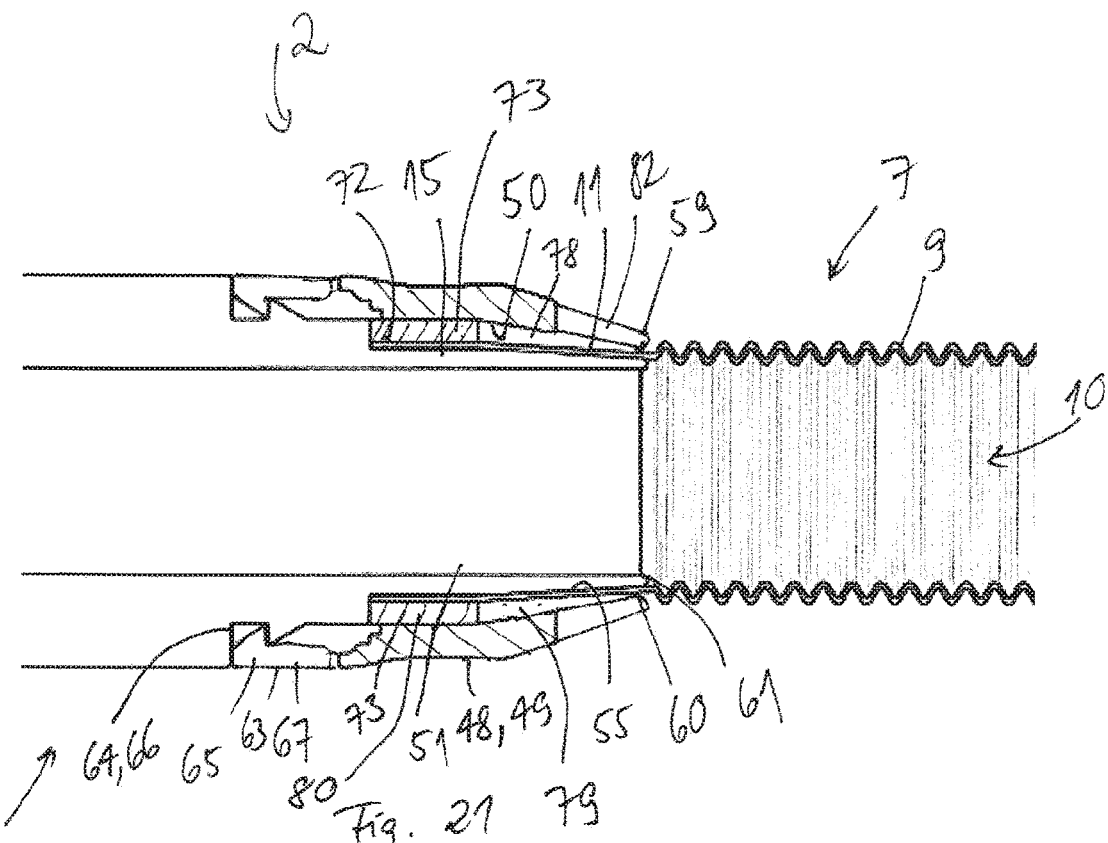
Figure 22:
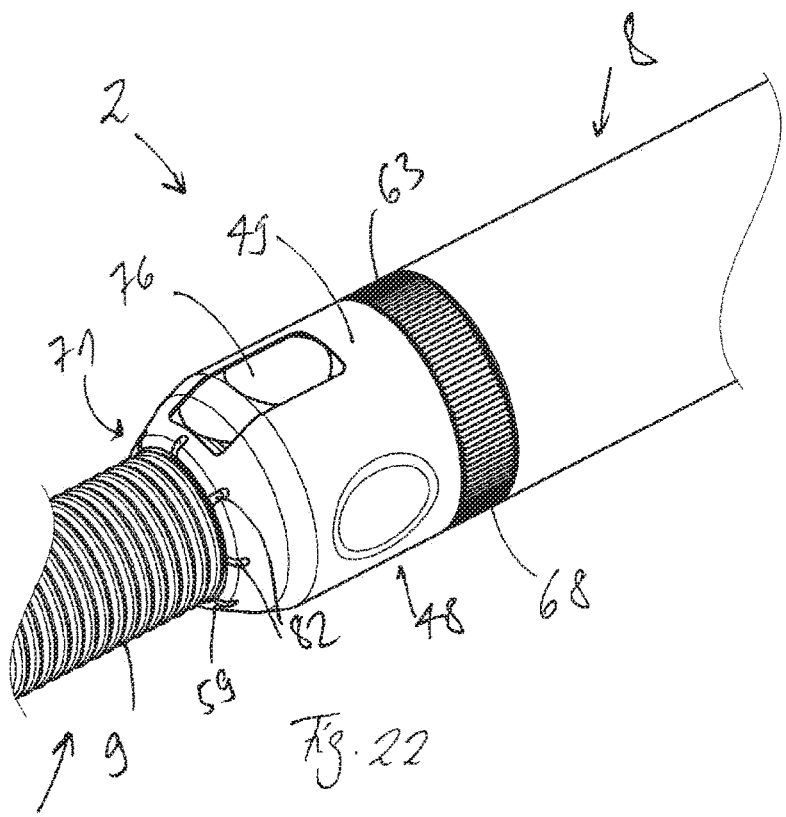
FIG. 22 shows a perspective illustration of a further exemplary embodiment of a cannula system of the type proposed here in a connected state.
Figure 23:
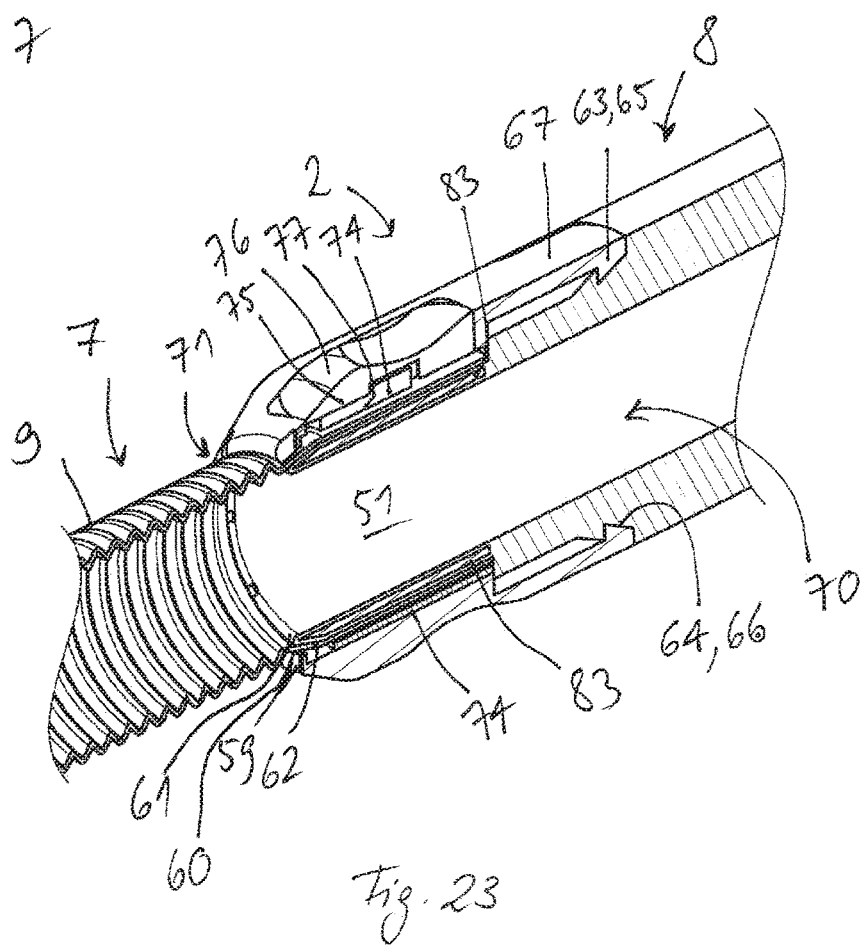
FIG. 23 shows a longitudinal section through the cannula system shown in FIG. 22 in the connected state.
Figure 24:
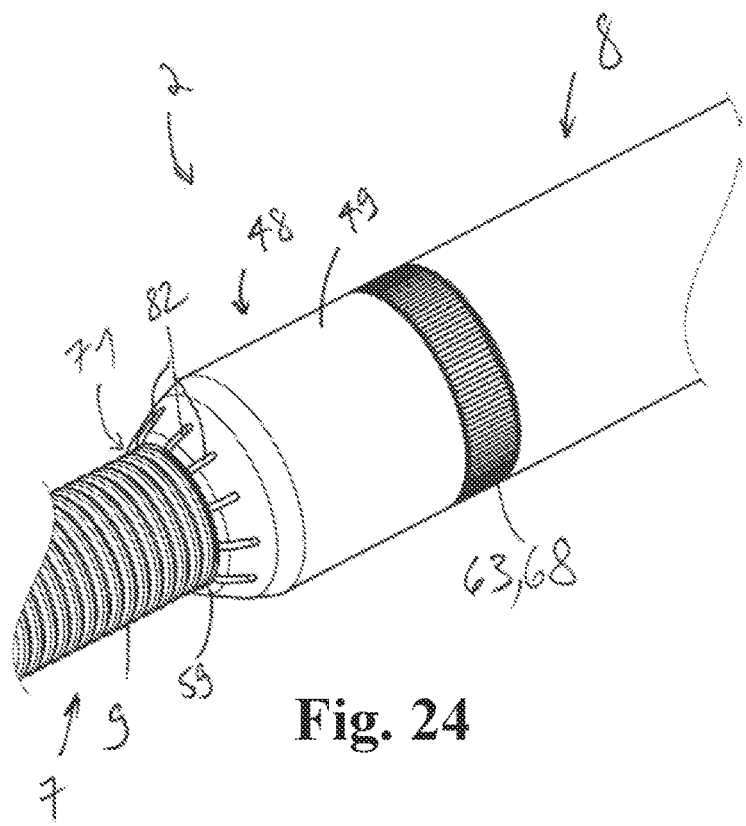
FIG. 24 shows a perspective illustration of a further exemplary embodiment of a cannula system of the type proposed here in a connected state.
Figure 25:
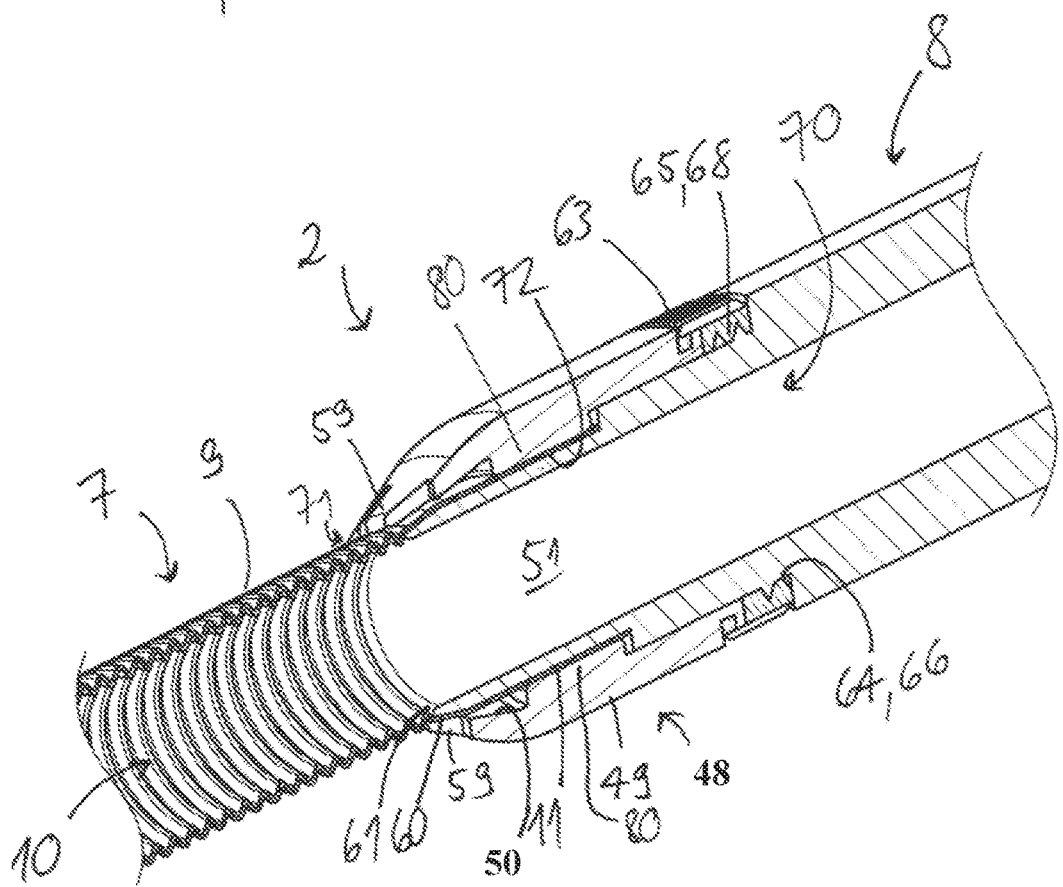
FIG. 25 shows a longitudinal section through the cannula system shown in FIG. 24 in the connected state.
Figure 26A:
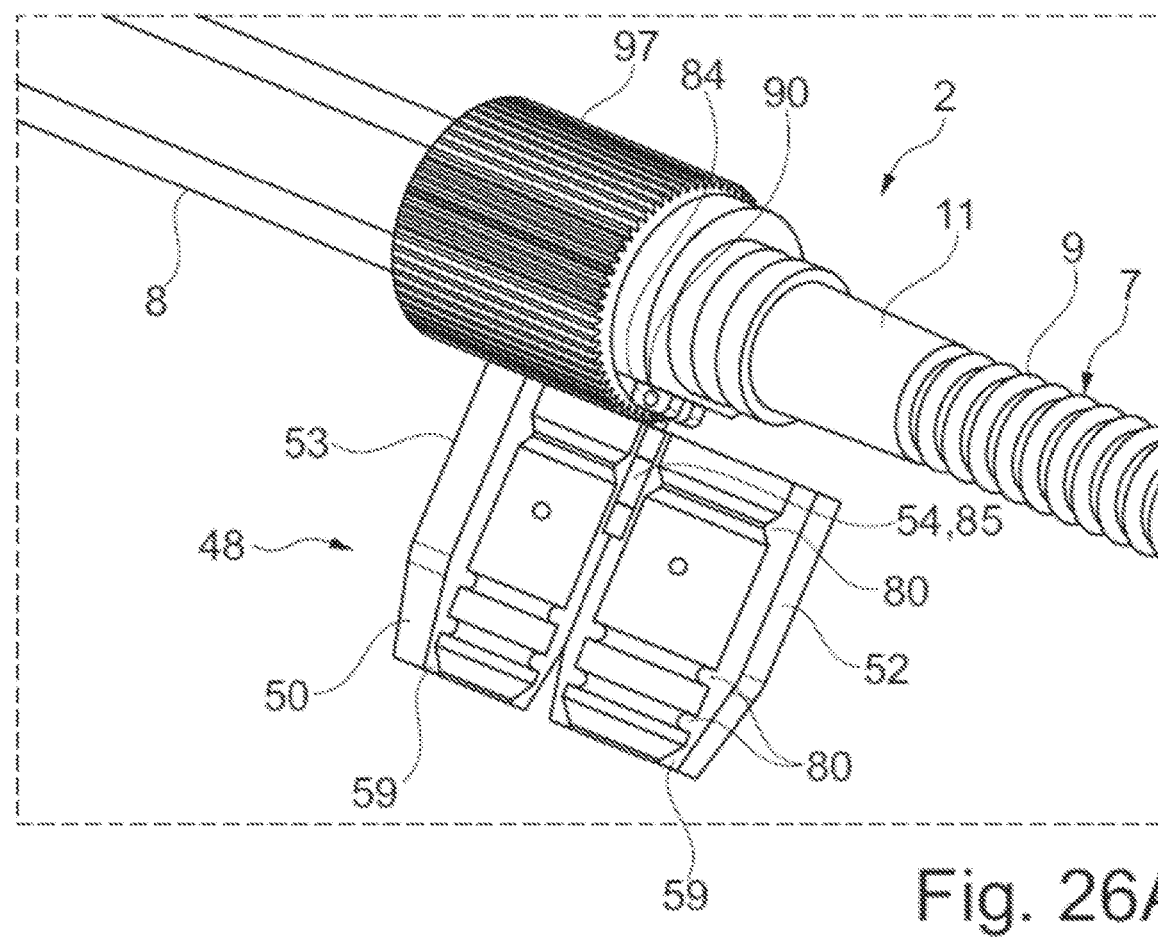
FIG. 26A.
Figure 26B:
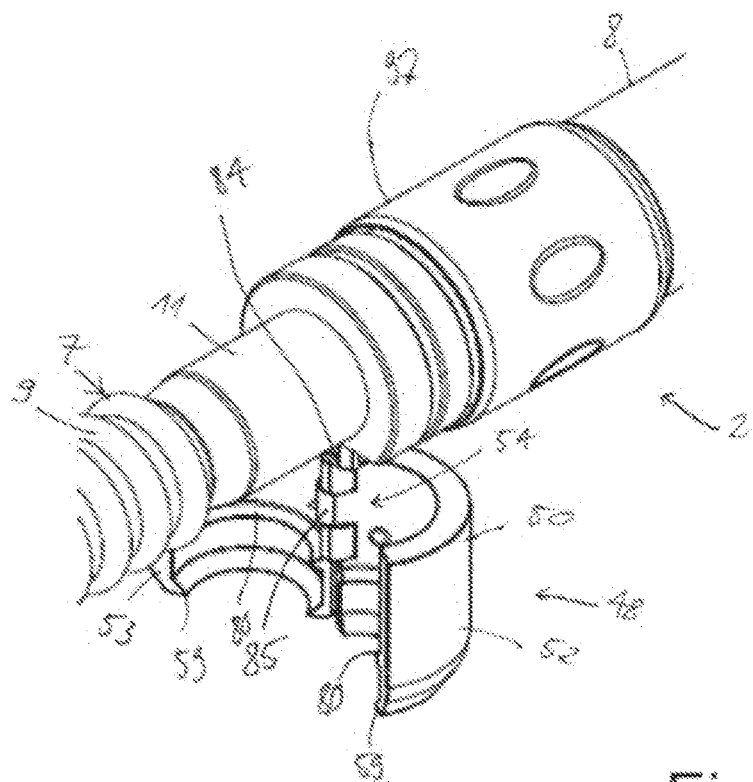
Figure 26C:
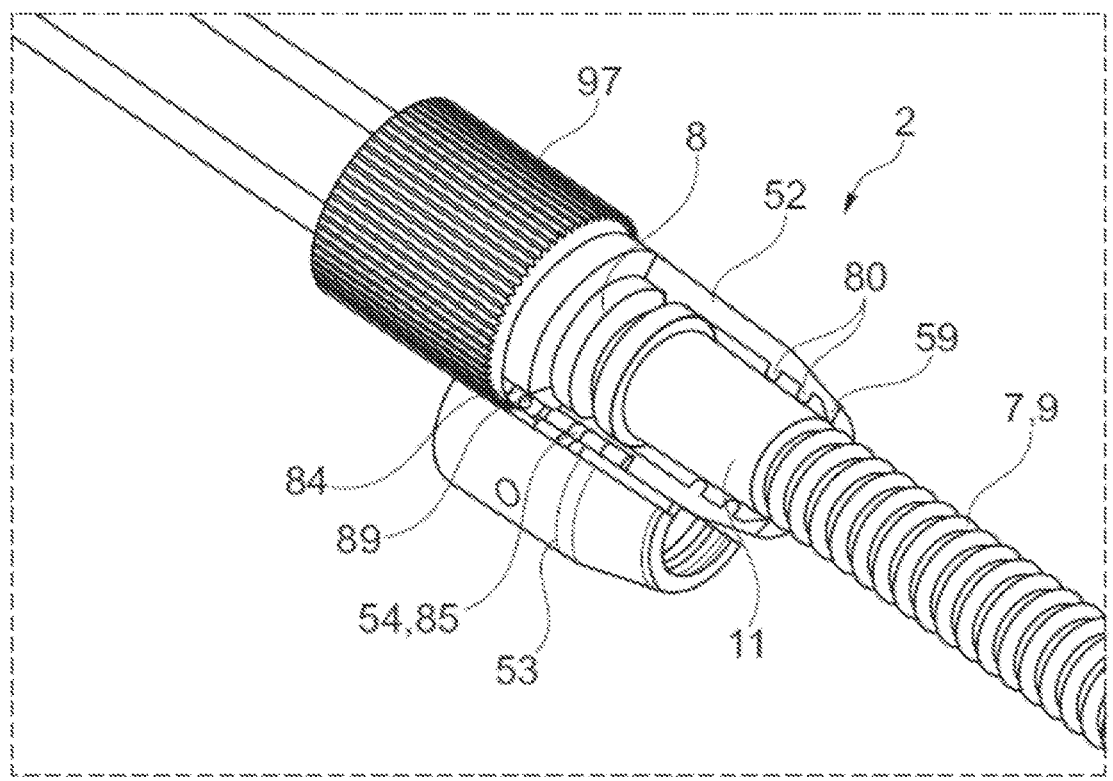
Figure 26D:
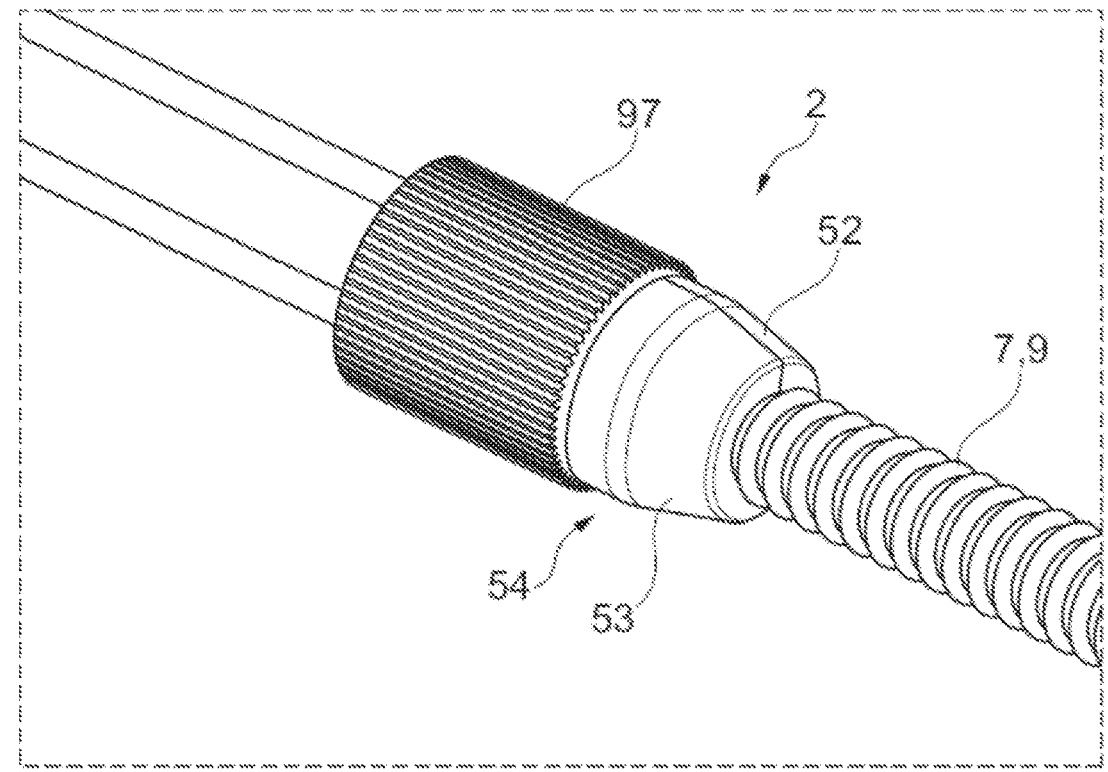
Figure 26E:
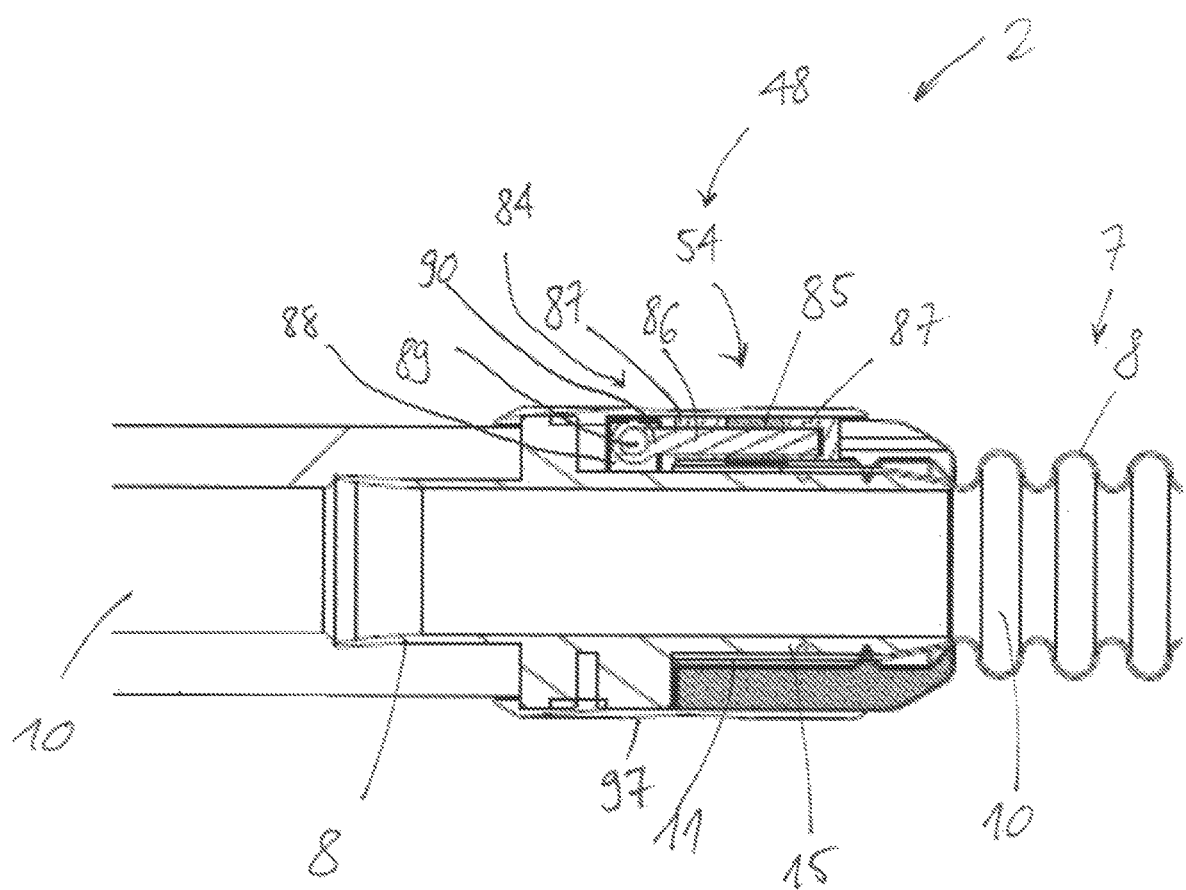
FIG. 26E shows a longitudinal section through the cannula system shown in FIG. 26D.
Figure 27A:
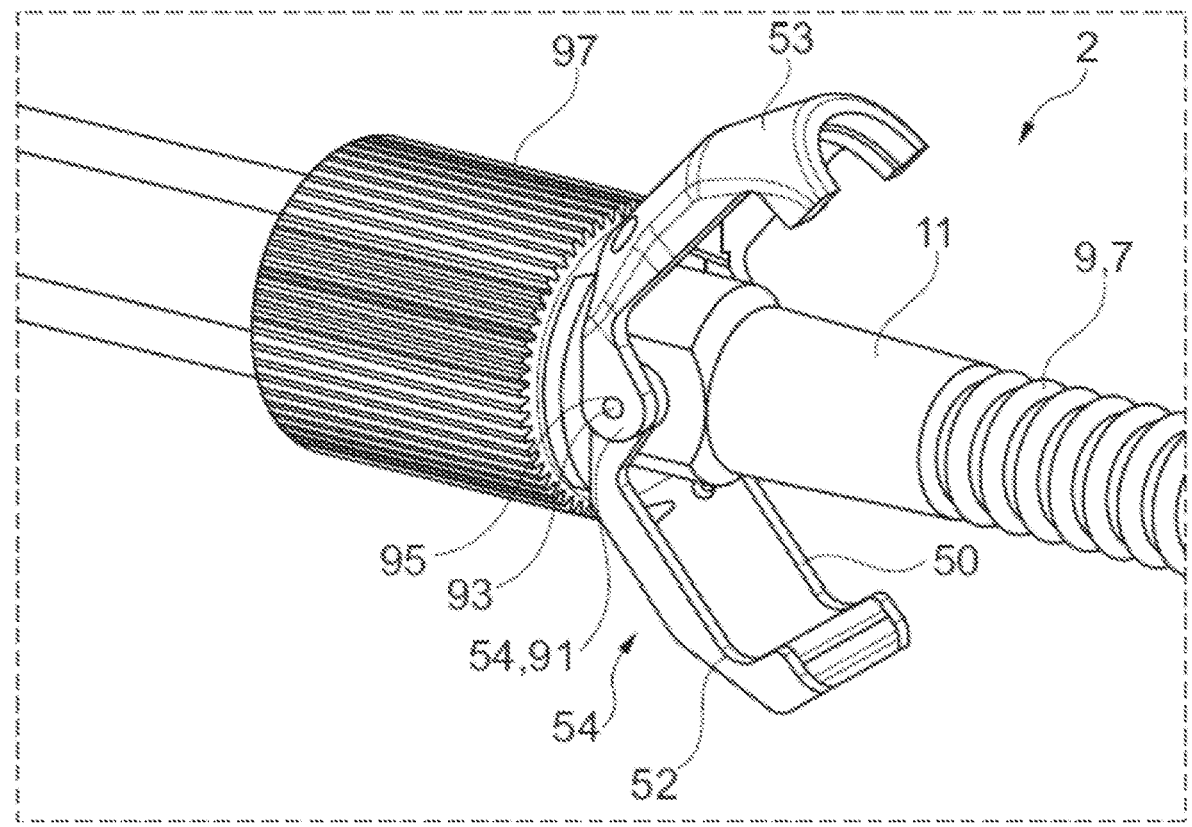
FIG. 27A shows a perspective illustration of an exemplary embodiment of a cannula system of the type proposed here, wherein the connector of the cannula system is connected.
Figure 27B:
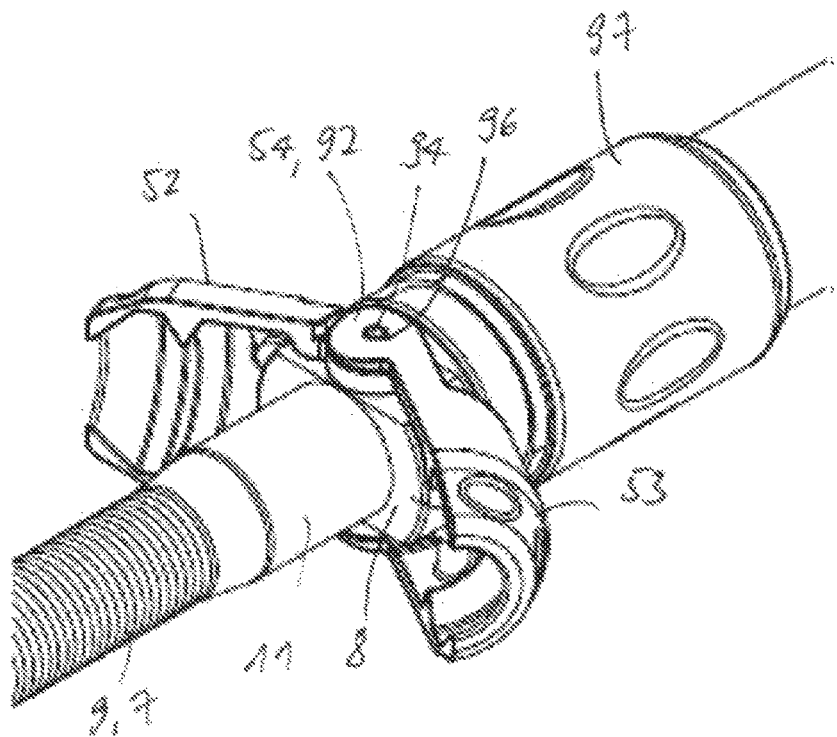
Figure 27C:
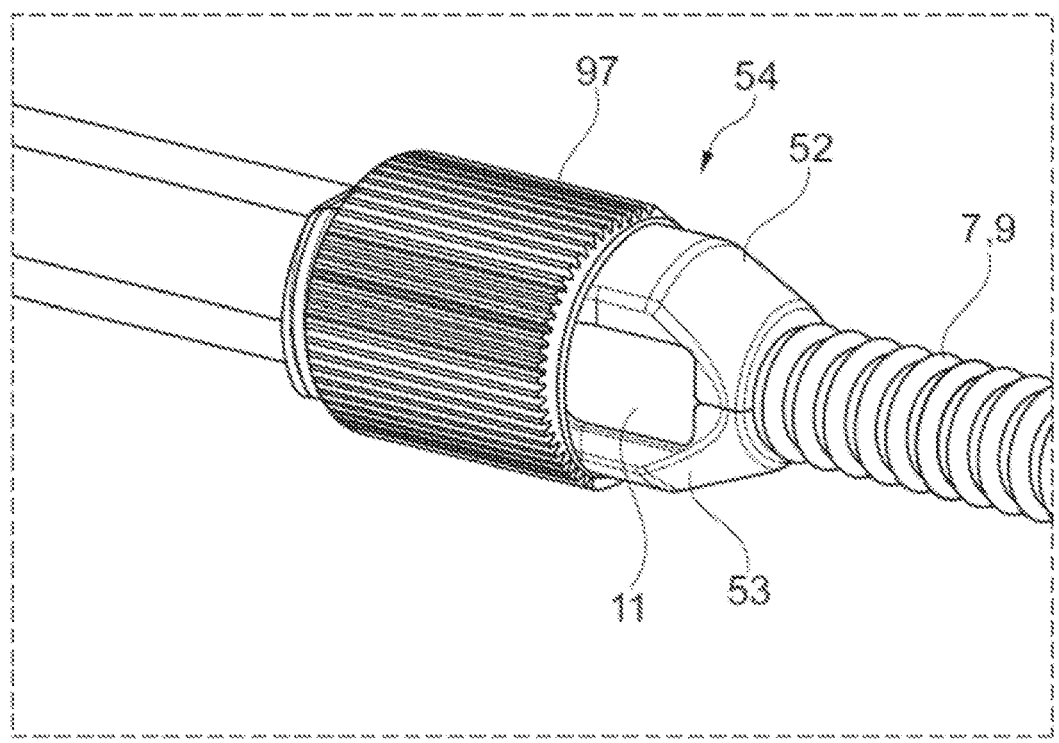
Figure 27D:
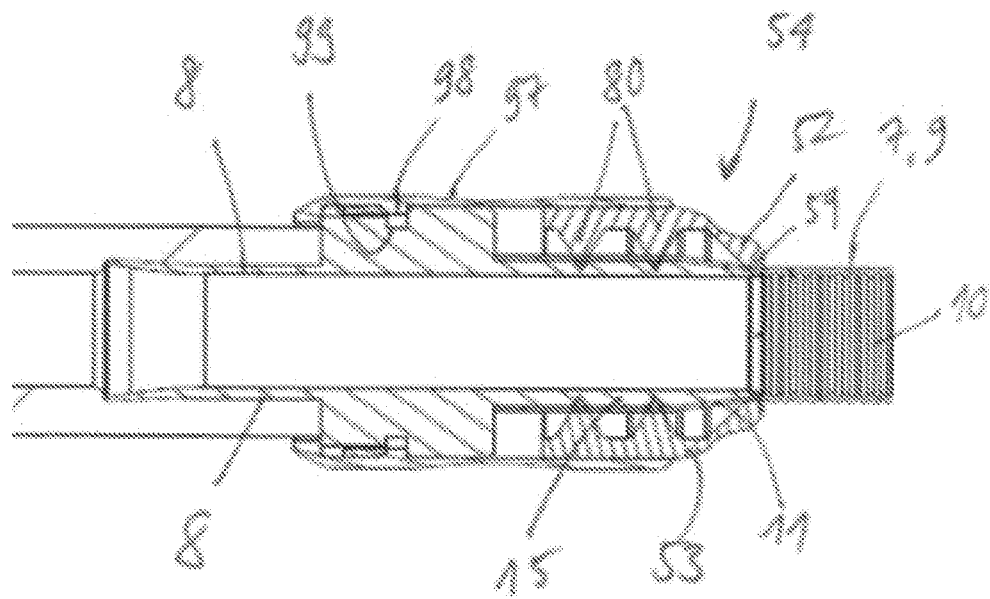

The cannula proposed here, the proposed cannula system and the proposed blood pump system, each comprising a tension ring, will be described hereafter in greater detail based on exemplary embodiments shown schematically in FIGS. 1 to 10. FIGS. 11 to 25 show further exemplary embodiments of the proposed cannula system, each without tension ring. In the drawings:

FIG. 1 shows a perspective illustration of a blood pump system of the type proposed here;

FIG. 2 shows the blood pump system shown in FIG. 1 in a view from above;

FIG. 3 shows the blood pump system shown in FIG. 1 in a sectional illustration;

FIG. 4A shows a cannula system of the blood pump system shown in FIG. 1 in a longitudinal sectional illustration;

FIG. 4B shows a variant of the cannula system shown in FIG. 4A in a longitudinal sectional illustration in a connected state:

FIGS. 5A, 5B shows a side view and a perspective view of a longitudinal section through the cannula system shown in FIG. 4A in a separated state;

FIG. 6A shows an operating element of a cannula of the cannula system shown in FIG. 4A in a sectional illustration and in a perspective illustration;

FIG. 6B shows an operating element of a cannula of the cannula system shown in FIG. 4B in a sectional illustration and in a perspective illustration;

FIG. 7A shows a hollow body of the cannula system shown in FIG. 4A in a collapsed axial view and in a longitudinal sectional illustration;

FIG. 7B shows a hollow body of the cannula system shown in FIG. 4B in a collapsed axial view and in a longitudinal sectional illustration;

FIG. 8 shows a sealing ring of the cannula system shown in FIG. 4A or in FIG. 4B in a longitudinal sectional illustration and in a perspective illustration;

FIG. 9 shows a tension ring of the cannula system shown in FIG. 4A or in FIG. 4B in a longitudinal sectional illustration and in a perspective illustration;

FIG. 10 shows a further sealing ring of the cannula system shown in FIG. 4A or in FIG. 4B in a longitudinal sectional illustration and in a perspective illustration;

FIG. 11 shows a perspective illustration of a cannula and of a hollow body separated therefrom of a cannula system of the type proposed here;

FIG. 12 shows a perspective illustration of the cannula shown in FIG. 10, wherein the hollow body is pushed into the channel of the cannula;

FIG. 13 shows a perspective illustration of the cannula shown in FIG. 11 and of the hollow body, which are connected by means of a connector of the cannula system;

FIG. 14 shows a perspective illustration of the cannula system of FIG. 13, wherein however one of two half shells of the connector is not shown;

FIG. 15 shows a longitudinal section through the cannula system of FIG. 13;

FIG. 16 shows a perspective illustration of the cannula system of FIG. 13, wherein the two half shells of the connector are pivoted apart;

FIG. 17 shows a longitudinal section through a modification of the cannula system of FIG. 13;

FIG. 18 shows a perspective illustration of a further exemplary embodiment of a cannula system of the type proposed here in a connected state;

FIG. 19 shows a longitudinal section through the cannula system shown in FIG. 18 in the connected state;

FIGS. 20, 21 show a longitudinal section through the cannula system shown in FIG. 18 with different axial positions of the connector;

FIG. 22 shows a perspective illustration of a further exemplary embodiment of a cannula system of the type proposed here in a connected state;

FIG. 23 shows a longitudinal section through the cannula system shown in FIG. 22 in the connected state;

FIG. 24 shows a perspective illustration of a further exemplary embodiment of a cannula system of the type proposed here in a connected state;

FIG. 25 shows a longitudinal section through the cannula system shown in FIG. 24 in the connected state;

FIG. 26 shows a perspective illustration of an exemplary embodiment of a cannula system of the type proposed here, wherein the connector of the cannula system is connected;

FIGS. 26B-D show further illustrations of the cannula system shown in FIG. 26A;

FIG. 26E shows a longitudinal section through the cannula system shown in FIG. 26D;

FIG. 27A shows a perspective illustration of an exemplary embodiment of a cannula system of the type proposed here, wherein the connector of the cannula system is connected;

FIGS. 27B-D show further illustrations of the cannula system shown in FIG. 27A; and FIG. 27D shows a longitudinal section through the cannula system shown in FIG. 27C.

Identical or mutually corresponding features are denoted by identical reference numerals in the figures and in the following description.

FIGS. 1 to 3 show a blood pump system 1 of the type proposed here, which comprises a cannula system 2 of the type proposed here and a blood pump 3. The blood pump 2 is implantable and comprises a pump housing 4 having a tubular pump inlet 5 and a tubular pump outlet 6.

The cannula system 2 comprises a cannula 7, which is configured as an implantable vascular prosthesis, and a hollow body 8, which in this example is provided by the tubular pump outlet 5.

As is shown in FIGS. 1 to 3 and in FIGS. 4A and 4B, the cannula 7 can be detachably connected to the hollow body 8 by means of a detent connection, as will be described in greater detail hereafter.

The cannula 7 comprises a hose element 9, which is made of a soft and elastic material, in the present example a graft material, for example, comprising a textile tubular carrier made of a polyester woven fabric (not shown). As is shown in FIGS. 4A and 4B, for example, the hose element 9 in the interior thereof defines a channel 10 for conducting blood.

As is also shown in FIGS. 4A and 4B, the hose element 9 includes a front end region 11, which defines a receiving region 12 for the hollow body 6 or the pump outlet 6 and at the foremost end 13 of which a front inlet opening 14 or a front opening 14 of the channel 10 is located. The channel 10 extends from the front end region 11 to a rear end region of the hose element 9. FIGS. 1 to 5B each show the hose element 9 only partially, so that the rear end region is not depicted. The rear end region of the hose element 9 can be connected, for example, to a blood vessel, for example by suturing to the blood vessel, if necessary using a suitable suture ring (likewise not shown).

As is shown in FIGS. 4A, 4B, 5A, 5B, 6A and 6B, for example, the hollow body 8 likewise includes a front end region 15, which is shaped and dimensioned so as to be pushable into the channel 10 of the hose element 9 through the front opening 14 of the channel 10, so that the front end region 15 of the hollow body 8 completely axially overlaps the front end region 11 of the hose element 9. In the shown example, the front end region 11 of the hose element 9 and the front end region 16 of the hollow body 8 have an axial extension equal in size. As is shown in FIG. 4A, the hollow body 8 likewise defines a channel 16 for conducting blood. In the pushed-in state shown in FIGS. 1 to 3, 4A and 4B, the channels 10, 16 of the hose element 9 and of the hollow body form 8 a continuous channel.

As is shown in FIGS. 1 to 5B and 7A and 7B, the hollow body 8 or the pump outlet 6 includes a stop 16 up to which the hollow body 8 or the pump outlet 6 can be pushed into the channel 10. The stop 16 thus defines a maximum axial depth which the hollow body 8 or the pump outlet 6 can be pushed into the channel 10. The stop 18 is configured, for example, in the form of a ridge-shaped widening 17 on an outer surface 18 of the hollow body 8 or pump outlet 6.

The cannula 7 moreover comprises a tension ring 19, which axially overlaps the front end region 11 of the hose element 9 within an axial overlapping region 20 and is fixedly connected to the front end region 11 of the hose element 9. The tension ring 19 is shown again separately in FIG. 9.

In a basic state of the cannula 7, in which no external forces act on the front end region 11 of the hose element 9 and on the tension ring 19, but only internal forces that are mutually exerted between these elements, the hose element 9 is preloaded by a radially outwardly directed (internal) force that is exerted by the tension ring 19 in the axial overlapping region 20 onto the front end region 11 of the hose element 9, and in particular onto the foremost end 13 of the hose element 9. In the basic state of the cannula 7, that is, in particular also when the hollow body 8 is not pushed into the front end region 11 of the hose element, as is shown in FIGS. 5A and 5B, for example, the front end region 11 is thus at least preloaded at the foremost end 13 of the hose element 8 by the tension ring 19. This preloading stabilizes the shape of the foremost end 13. Additionally, the foremost end 13 of the hose element 8 is elastically expanded by this preloading, so that a diameter of the front opening 14 of the channel 10 is increased, which in the shown example is radially circumscribed by the foremost end 13 of the hose element 9.

As is apparent from FIGS. 4A and 5A, for example, the tension ring 19 does not protrude axially beyond the front end region 11 of the hose element 9, and in particular thus does not axially forwardly beyond the foremost end 13 of the hose element 13, but ends thereon. The tension ring 19 extends circumferentially and concentrically around both the channel 10 in the axial overlapping region 20 and the hose element 9. As is apparent from FIG. 5B, for example, a radially inner surface 21 of the tension ring 19 abuts a radially outer surface 22 of the hose element 9. In this example, the tension ring 19 is thus disposed outside the channel 10. However, in principle, it would also be possible for a radially outer surface 23 of the tension ring 19 to abut a radially inner surface 24 of the hose element 9. In this example, the tension ring 19 would thus be (at least partially) disposed inside the channel 10.

In the basic state, an inside diameter of the hose element 9, and in particular a smallest inside diameter of the hose element 9, increases within the front end region 11 toward the front opening 14 of the channel 10. For example, in the basic state of the cannula 7, the smallest inside diameter of the hose element increases within the front end region 11 increases toward the tension ring 19 (see FIGS. 4A and 5A, for example).

In the shown example, in the basic state of the cannula 7, a diameter of the front opening 14 of the channel 7, that is a (smallest) inside diameter $D_I$ of the foremost end 13 of the hose element 9, is greater than a largest outside diameter $D_A$ of the hollow body 8 in the front end region 15 of the hollow body 8, $D_A < D_I$. In this way, an insertion of a foremost end 25 of the hollow body 8 into the front opening 14 of the channel 10 of the hose element 9 is simplified. When the front end region 15 of the hollow body 8 is completely, that is, as far as the stop 16 allows, pushed into the channel 10, a free space 27 in the form of an annular gap, which extends around the hollow body 8 inside the channel 10 in an annular manner, exists in the axial overlapping region 20 between the inner surface 24 of the hose element 9 and an outer surface 26 of the front end region 25 of the hollow body 8 (see FIGS. 4A and 4B, for example).

As is shown in FIGS. 4A, 4B, 5A and 5B, the cannula 7 moreover comprises a sealing ring 28 axially overlapping the front end region 11 of the hose element 9. The sealing ring 28 is disposed axially behind the tension ring 19 and axially spaced apart therefrom. In the shown example, an axial position of a rear end 29 of the sealing ring 28 coincides with an axial position of a rear end 30 of the front end region 11 of the hose element 9. Moreover, the sealing ring 28 extends circumferentially and concentrically around the channel 10. Moreover, a radially inner surface 31 of the sealing ring 28 abuts a radially outer surface 32 of the hose element 9. The sealing ring 28 is displaceable and rotatable relative to the hose element 9.

In the basic state of the cannula 7, in which also no external forces act on the sealing ring 28, the inside diameter $D_I$ of the hose element 9 at the tension ring 19 is greater than an inside diameter $D_i$ of the hose element 9 at the sealing ring 28. The described inside diameters $D_I$, $D_i$ are each the smallest inside diameter in the respectively viewed axial region.

As is clearly apparent in the illustrations of the sealing ring 28 shown in FIG. 8, the sealing ring 28 widens toward the front in the basic state, that is, toward the foremost end 13 of the hose element 8 and tapers correspondingly in the opposite direction. The inner surface 31 of the sealing ring 28 (that is, the radially inner surface thereof) has a conical shape, for example.

As is apparent in FIGS. 4A and 4B, the sealing ring 28 is disposed so as to axially overlap the end region 15 of the hollow body 8, which is pushed into the channel 10 up to the stop 16, in an axial overlapping region 33. In this axial overlapping region 33, a mutual (radial) pressing force, which is caused by the sealing ring 28, exists between the hose element 9 and the inserted hollow body 9, whereby (radial) sealing is effectuated between the hollow body 8 and the hose element 9. The intensity of this mutual pressing force is adapted by a suitable selection of the inside diameter $D_I$ of the sealing ring, the outside diameter $D_A$ of the front end region 15 of the hollow body 8 in the axial overlapping region 33, and the strength of the sealing ring 28.

The front end region 15 of the hollow body 8 pushed into the channel 9 up to the stop 16 does not protrude beyond the rear end 29 of the sealing ring 28, but ends at the rear end 29 of the sealing ring 28 that is, at the rear end of the above-described axial overlapping region 33. In this way, blood is prevented from flowing between the hose element 9 and the hollow body 8 (pocket formation of the hose element), whereby the risk of the development of thrombi is reduced.

The cannula 7 moreover comprises an operating element 34 having a sleeve-shaped base body 35. The sleeve-shaped base body 35 comprises an outer grip surface 36 and defines an interior region 37 (see FIGS. 6A and 6B, for example, which show the operating element 34 separately). As is shown in FIGS. 3, 4A, 4B, 5A and 5B, the front end region 11 of the hose element 9, the tension ring 19 and the sealing ring 28 are received in the interior region 37. For this purpose, the sleeve-shaped base body 35 comprises receiving regions 38, 39 for the tension ring 19 and for the sealing ring 28 on an inner surface defining the interior space. These receiving regions 38, 39 are defined, for example, by annular grooves or by radially inwardly protruding indentations of the sleeve-shaped base body 35.

Moreover, the operating element 34 comprises several detent elements 40 configured as detent arms, which protrude axially from a front end of the sleeve-shaped base body 35 in a cantilevered manner beyond the front end region 11 of the hose element 9 (see FIG. 3, for example). Each of the detent elements 40 comprises a radially inwardly directed detent tooth 41, which is configured to form a detent connection with a corresponding mating detent element 42 of the hollow body 8 as soon as the hollow body has been pushed into the channel 10 up to the stop 16. In this example, these mating detent elements 42 are configured as detent surfaces 43 on the surface 18 of the hollow body 8, in the present case on the widening 17 which forms the stop 16, for example (see FIGS. 7A and 7B, for example).

In the example shown in FIG. 7A, these detent surfaces 43 are rounded, as are the corresponding detent teeth 42 shown in FIG. 6A. Such a rounded shape of these detent partners, as well as a likewise possible chamfer, allows the detent connection to be released by axially pulling the cannula 7 and the hollow body 8 apart.

In contrast, these detent surfaces 43, as well as the corresponding detent teeth 42 shown in FIG. 6B, are designed to have sharp edges in the axial direction in the variant of the hollow body 8 shown in FIG. 7B. Releasing the detent connection in this variant thus also requires a rotational movement of the cannula 7 with respect to the hollow body 8, in addition to the relative axial pulling apart movement. As a result of this relative rotational movement, which in the present example is by approximately 30° proceeding from a stable detent position, the detent teeth 41 glide over the detent surfaces 43, whereby the detent elements 40 are radially forced apart to such an extent that these can be pulled off axially over the widening 17.

In the illustrations of the tension ring 19 shown in FIG. 9, it is apparent that the tension ring includes multiple through-holes 44. In the example of the cannula 7 described here, a sewing thread (not shown) extends through these holes, which is used to sew the tension ring 19 to the hose element 9. In addition, or as an alternative, it would also be possible to fixedly join the tension ring 19 to the hose element by adhesive bonding or fusing.

The tension ring 19 is more rigid in this example than the hose element 9, and also more rigid than the sealing ring 28. For this purpose, the tension ring 19 is made of a stronger material than the hose element 9 and than the sealing ring 28, for example.

In the shown exemplary embodiment, the cannula 7 moreover comprises an optional further sealing ring 45, which is shown again separately in the illustrations shown in FIG. 10 for the sake of clarity. This further sealing ring 45 is preferably disposed axially in front of the tension ring 19 and coaxially with respect to the tension ring 19 and the first sealing ring 28. In addition, the further sealing ring 45 is disposed, for example, inside the interior region 37 of the hollow body 35. In connected state, that is, when the hollow body 8 is inserted into the channel 10 up to the stop 16, as is shown in FIGS. 4A and 4B, the further sealing ring 45 is disposed axially between the stop 16 and the tension ring 19 and concentrically extends around the channel 16 of the hollow body 8.

The tension ring 19, the sealing ring 28 and the further sealing ring 45 are each made of a hemocompatible material, for example each being made of a polymer, such as a silicone. The operating element 34 is likewise made of a hemocompatible material, such as a stainless steel or a titanium alloy.

As soon as the above-described detent connection between the cannula 7 and the hollow body 6 has been established, the stop 16 and the tension ring 19 each press axially against the sealing ring 45, so that the sealing ring 45 effectuates additional sealing of the connection. The further sealing ring 45 is made of the same material as the first sealing ring 28, for example.

In principle, however, the cannula 7 proposed here can also be configured without the further sealing ring 45. It may then be provided, for example, that the hollow body 8 is inserted into the channel until the tension ring 19 makes contact with the stop 16, and optionally presses axially thereagainst, when the detent connection has been established.

In principle, the proposed cannula 7 can furthermore comprise a kink guard, which can be attached, for example, to a rear end of the operating element 34 or the sleeve-shaped base body 35 thereof.

In addition to the advantage that the shown cannula system 2 allows a connection to be manually established easily and securely between the cannula 7 and the hollow body 8, moreover an excellent gentle design for the blood is achieved in that the blood is only in contact with few different materials. As is apparent particularly well from FIG. 3, the hollow body 8, that is, the pump outlet 6, preferably opens directly into a pump chamber 46 of the blood pump 3. For example, the pump rotor of the blood pump 3 is disposed in the pump chamber 46. In the shown example, the pump chamber 46, as well as the pump inlet 5 and the pump outlet 6, are defined by the outside wall of the pump housing 4. The channel 16 of the pump outlet 6 and the pump chamber 46 are thus circumscribed by the same material, for example a biocompatible material such as stainless steel or titanium. From the channel 16 of the pump outlet 6, the blood directly enters the channel 10 of the hose element 9 of the cannula 7, during this transition thus only coming in contact with the material of the pump outlet 6 and the material of the hose element 9, and with no other materials.

In the example shown in FIG. 3, the pump chamber 46 is configured in the shape of a spiral chamber widening toward the pump outlet 6, wherein the longitudinal axis of the pump outlet 6 extends perpendicularly to the rotational axis of the pump rotor and, additionally, is laterally offset from this rotational axis (tangential outlet). Other configurations of the blood pump 3 are also possible, of course.

FIG. 11 shows a cannula 7 and a hollow body 8, separate therefrom, of a cannula system of the type proposed here. In contrast to the cannula systems 2 shown in the preceding FIGS. 1 to 10, the cannula 7 shown in FIG. 11 is formed completely by the hose element 9. Thus, reinforcing elements and tensioning elements, and thus in particular a tension ring, are absent in this cannula 7. A hose element 9 of the cannula 7 essentially corresponds to the hose element 9 from the preceding examples, thus being made of a graft material comprising a tubular textile carrier, which is made of a polyester woven fabric, for example, and sealed by way of a coating, for example using gelatin. The hose element 9 includes a front end region 11 and a rear end region (not shown), wherein a channel 10 (see FIG. 15, for example) extends from the front end region 11 of the hose element 9 to the rear end region of the hose element 9 through the hose element 9.

Similarly to the hollow bodies 8 shown in FIGS. 1 to 10, a hollow body 8 likewise shown in FIG. 11 likewise includes a front end region 15, which can be inserted into the channel 10 of the hose element 9 through a front inlet opening 14 of the channel 10, as is shown in FIG. 12. The front end region 11 of the hose element 11 is slightly expanded, whereby the corrugated profile of the hose element is reduced or entirely eliminated. The hollow body 8 is a further hose element, for example. However, the hollow body 8 could also be a pump outlet or a pump inlet of a blood pump, for example the pump outlet 6 of the blood pump 3 shown in FIGS. 1 to 3. For example, in particular in the exemplary embodiments shown in FIGS. 26A to 27D, the hollow body may also be the pump outlet 6 of the blood pump 3 shown in FIGS. 1 to 3 or another tube element, which may be composed of a metallic material such as titanium, a titanium alloy, or stainless steel.

In addition to the cannula 7 and the hollow body 8 already shown in FIGS. 11 and 12, FIG. 13 moreover shows a connector 48 of a cannula system 2 of the type proposed here. The connector 48 is configured, in the connected state of the cannula system 2 shown in FIG. 13, to receive the front end region 11 of the hose element 9 and the front end region 15 of the hollow body 8 inserted into the channel 10 in an interior region 51 of the connector 48, as is the case in FIGS. 14 to 17, for example. The front end region 15 of the hollow body 8 and the connector 48 are configured, in the connected state of the cannula system 2, to exert clamping forces onto the front end region 11 of the hose element 9, and to clamp the front end region 11 of the hose element 9 between the front end region 15 of the hollow body 8 and the connector. The front end region 15 of the hollow body 8 and the connector 48 are thus configured to clamp the front end region 11 of the hose element 9 between the front end region 15 of the hollow body 8 and the connector 48, so that undesired separation of the cannula or of the hose element from the hollow body, for example by axial tensile forces, can be avoided. By suitably configuring a radially outer surface 55 of the front end region 15 of the hollow body 8 and the inner surface 50 of the connector 48, which circumscribes the interior region 51 or cavity 51 of the connector 48, it is possible to accordingly predefine the clamping forces.

The connector 48 comprises a base body 49, which has a sleeve-shaped or collar-shaped configuration, for example, and surrounds the interior region or the cavity of the connector 48. As is apparent from FIGS. 14 and 17, for example, the base body 49 includes a (radially) inner surface 50, which radially circumscribes the interior region (cavity) 51 of the connector 48.

The cannula systems 2 shown in FIGS. 18 to 25 and FIGS. 26A to 27D comprise corresponding or similar cannulas 7, hollow bodies 8 and connectors 48 as the cannula system 2 described based on FIGS. 11 to 17. So as to avoid unnecessary repetitions, the features of the cannula systems 2 shown in FIGS. 18 to 25 and in FIGS. 26A to 27D which essentially correspond to those of the cannula system shown in FIGS. 13 to 17 will thus not be described again. Additional features that are shared by multiple exemplary embodiments will be described simultaneously hereafter with respect to multiple exemplary embodiments. In particular, the differences between the shown cannula systems 2 will be addressed in greater detail.

The base body 50 shown in FIGS. 13 to 17 has a two-piece design and is formed by two half shells 52, 53, which are pivotably connected to one another by a joint 54 designed as a hinge. The two half shells can be pivoted about a pivot axis formed by the joint 54 into an open configuration, see FIG. 16, and into a closed configuration, see FIG. 13. The two half shells 52, 53 are configured, for example, to surround the interior region 51 of the connector 49 in the closed configuration, and to exert clamping forces on the front end region 11 of the hose element 8 in the connected state of the cannula system 2. In the open configuration, the two half shells can be pivoted apart from one another so as to define a lateral opening through which the front end region 11 of the hose element 9 of the cannula 2 and the front end region 15 of the hollow body 8 which is inserted into the channel 10 can be pushed from the outside between the two half shells 52, 53. As is shown in FIG. 16, it is possible, first, to place one of the half shells 52, 53 onto the front end region 11 of the hose element 1 and the inserted front end region of 15 the hollow body 8 and thereafter, by pivoting the other half shell 53, to bring also this other half shell 53 in contact with the front end region 11 of the hose element 9 or to place the other half shell thereon. By further compressing the two half shells, this pivoting movement can be continued until, ultimately, the closed configuration of the half shells is achieved, as is shown in FIG. 13, and the above-described clamping forces are generated, so that ultimately the connected state of the cannula system is achieved. The connected state can thus be achieved without axial displacement of the connector, so that advantageously creasing of the hose element can be prevented or at least reduced. Moreover, an improved visual inspection of the hose element during connection is possible, as is shown in FIG. 16.

The connector 48 further comprises a closure device 56, which is configured to hold the two half shells 52, 53 in the closed configuration. The closure device 56, for example, comprises detent elements 57, 58, which are configured, for example, as one detent element on the one half shell and a corresponding mating detent element on the other half shell. These detent elements are configured, for example, to engage in the closed configuration of the half shells 52, 53, when the two half shells are pivoted from the open configuration into the closed configuration.

The connectors 48 shown in FIGS. 18 to 25 each have a one-piece sleeve-shaped base body 49. These base bodies 48 each have a front opening 70 and a rear opening 71, which each form an access to the interior region (cavity) 51 of the connector 48. In a force-free basic state of the hose element 8, the hose element 8 of the cannula 7 has a largest outside diameter which is smaller than a smallest inside diameter of the front opening 70, smaller than a smallest inside diameter of the rear opening, 71 and smaller than a smallest inside diameter of the interior region 51 of the connector 48. In this way, the connector 48 and the base body 49 thereof can be axially freely displaced relative to the hose element 9 up to the front end region 11 of the hose element 9.

In the cannula systems 2 shown in FIGS. 18 to 21, 24 and 25, it may be provided that, with further axial displacement, contact occurs, in the front end region 11 of the hose element 9 when the hollow body 8 is inserted therein, as shown, between the outer surface 72 of the front end region 11 of the hose element 9 and, in the case of the example shown in FIGS. 24 and 25, the inner surface 50 of the connector 48 or, in the case of the example shown in FIGS. 18 to 21, of a flexible element 73, which is disposed radially between the inner surface 50 of the base body 48 and the outer surface 72 of the front end region 11 of the hose element 9. Further axial displacement of the connector 48 ultimately generates the described clamping forces. For this purpose, an outside diameter of the front end region 15 of the hollow body 8 increases from the foremost edge 61 toward the rear in these examples.

In the cannula system 2 shown in FIGS. 22 and 23, the clamping force is generated by means of a clamping sleeve 74. The clamping sleeve 74 is made, for example, of an elastic material, such as titanium or a titanium alloy. The clamping sleeve 74 includes a longitudinal slot 77 extending across the entire axial length of the clamping sleeve 74. The clamping sleeve 74 is disposed in the interior region 51 of the connector 48 and configured, in the connected state of the cannula system 2, to enclose the front end region 11 of the hose element 9 and evoke a clamping force to be exerted on the front end region 11 of the hose element 9. The connector 48 comprises a wedge element 75, wherein the wedge element 75 and the clamping sleeve 74 can be moved relative to one another between a preloaded configuration and a released configuration. In the preloaded configuration, the wedge element 75 is pushed into the longitudinal slot 77 of the clamping sleeve 74, so that the clamping sleeve 74 is elastically preloaded and radially expanded by the wedge element 75. In the released configuration, the clamping sleeve 74 is not preloaded and expanded by the wedge element 75. The wedge element 74 and the clamping sleeve 74 can be moved from the preloaded configuration into the released configuration when the cannula system is to be transferred into the connected state, in which the clamping sleeve generates the described clamping forces in the released configuration. In the preloaded and expanded state, the clamping sleeve 74 has a smallest inside diameter which is greater than a largest outside diameter of the front end region 11 of the hose element 8, even when the hollow body 8 is inserted therein, as shown. In this way, the clamping sleeve thus expanded is axially displaceable with respect to the front end region 11 of the hose element 8 up to a desired end position, and can be released in this end position for the generation of the clamping forces.

The connector 48 further comprises an operating element 76 which can be moved between a first position and a second position and forms an outer operating surface of the connector 48, which can be manually operated by a user so as to move the operating element 76 between the first and second positions. For this purpose, the operating element 76 is rigidly connected to the wedge element, for example.

In each of the exemplary embodiments described based on FIGS. 11 to 25, it is provided that the cannula system comprises a flexible element 73, which is designed to abut the front end region 11 of the hose element 8 within the interior region 51 of the connector 48 in the connected state of the cannula system 2, and to transmit at least a portion of the clamping forces onto the front end region of the hose element.

In the cannula system 2 shown in FIGS. 18 to 23, the flexible element 73 has already been described above. In this example, the flexible element 73 is disposed radially outside the hose element 9 so as to transmit radially inwardly directed clamping forces from portions of the base body located further to the radial outside, inwardly onto the hose element. In this cannula system 2 and in the cannula system 2 shown in FIGS. 24 and 25, the hollow body 8 is made of a hard material, for example, so as to serve as a counter bearing for the clamping forces, for example made of a metallic material, such as a titanium alloy or a stainless steel.

In the cannula system 2 shown in FIGS. 11 to 17 and 22 to 23, the flexible element 73 is disposed radially inside the hose element 9 so as to transmit radially outwardly directed clamping forces originating from the hollow body 8 onto the hose element 9. In these cannula systems, the hollow body 8 is made of a soft material, such as a silicone or another flexible polymer, at least in some regions. The flexible element 73 forms a radially outer subregion of the front end region 15 of the hollow body 8. In the cannula systems 2 shown in FIGS. 11 to 17 and 22 to 23, the front end region 15 of the hollow body 8 comprises a reinforcing sleeve 83, which is made, for example, of a preferably strong material, for example of a metallic material, such as stainless steel or titanium or a titanium alloy. The reinforcing sleeve 83 is disposed, for example, radially inside the flexible element 73 and embedded in the silicone of the respective hollow body 8 of these examples. The reinforcing sleeve 83 is used to absorb a clamping force that is introduced from radially outside and forms a counter bearing for the connector 48.

In the shown examples, it is provided that the flexible element 73 deforms in some regions given the flexibility thereof and conforms to abutting surfaces of the hose element 9, of the hollow body 8 or of the base body 49, when the clamping forces are applied thereto. The deformations effectuate an improved sealing action, for example. The flexible element can be made of silicone or another flexible polymer, for example.

In the cannula system shown in FIGS. 18 to 21, the flexible element 73 is configured as a sleeve which is detachable from the hose element 9, from the hollow body 8 and from the connector 48 and freely displaceable along the hose element 9 and which, in the force-free basic state thereof, has a sufficiently large inside diameter for this purpose. In the force-free basic state of the sleeve, the inside diameter and an outside diameter of the sleeve decrease from a front end of the sleeve facing the hollow body toward a rear end of the sleeve facing the hose element. For example, the sleeve includes a conically shaped rear subregion 79. Moreover, it comprises a rear axial subregion 79 having multiple axial slots 78 and a non-slotted front axial sub-segment 80.

The base body 50 of the connector 48 of the cannula system 2 shown in FIGS. 26A to 26E and the base body 50 of the connector 48 of the cannula system 2 shown in FIGS. 27A to 27D are, as with the base body 50 of the connector 48 of the cannula system 2 shown in FIGS. 13 to 17, each have a two-piece design and are formed by two half shells 52, 53 which are connected to one another by at least one joint 54. The two half shells can be pivoted about a (first) pivot axis formed by the at least one joint 54 into an open configuration, see FIGS. 26A to 26C or 27A and 27B, and into a closed configuration, see FIGS. 26D and 26E or 27C and 27D. The two half shells 52, 53 are configured, for example, to surround the interior region 51 of the connector 49 in the closed configuration, and to exert clamping forces on the front end region 11 of the hose element 8 in the connected state of the cannula system 2.

In the exemplary embodiment shown in FIGS. 26A to 26E, the two half shells 52, 53 can, in the open configuration, be pivoted apart from one another so as to define a lateral opening so that the two half shells, the front end region 11 of the hose element 9 of the cannula 2, and the front end region 15 of the hollow body 8 inserted into the channel 10 can be received from the outside between the two half shells 52, 53 through the lateral opening by way of the two half shells being pivoted about a further (second) pivot axis, as described hereafter. As is shown in FIG. 26C, it is possible, first, to place one of the half shells 52, 53 onto the front end region 11 of the hose element 1 and the front end region of 15 the hollow body 8 and thereafter, by pivoting the other half shell 53 about the (first) pivot axis, to bring also this other half shell 53 in contact with the front end region 11 of the hose element 9 or to place the other half shell thereon. By further compressing the two half shells 52, 53, this pivoting movement can be continued until, ultimately, the closed configuration of the half shells is achieved, as is shown in FIG. 26D, and the above-described clamping forces are generated, so that ultimately the connected state of the cannula system is achieved.

In the exemplary embodiment shown in FIGS. 26A to 26E, the connector 48 comprises a further (second) join 84 which forms a further (second) pivot axis which is different from the pivot axis of the (first) joint 54 already mentioned above. For example, the two half shells 52, 53 are fixedly connected to the hollow body 8 via the further joint 54 and are pivotable relative to the hollow body 8 about the at least one further (second) pivot axis in the manner described above. In the example shown, the further pivot axis extends within a plane which is oriented essentially perpendicular to a longitudinal axis of the hollow body 8 and additionally essentially perpendicular to the pivot axis of the (first) joint 54. The joint 54 may be moved from a first position, see FIGS. 26A and 26B, into a second position, see FIGS. 26C to 26E, and back, by pivoting the half shells 52, 53 about the further (second) pivot axis. For example, the (first) pivot axis of the (first) joint 54 is, in the second position, oriented essentially parallel to the longitudinal axis of the hollow body and extends, in the first position, within a plane which is oriented essentially perpendicular to the longitudinal axis of the hollow body 8. In the first position, the (first) joint 54 and the half shells 52, 53 are pivoted away from the hollow body 8 such that it is freely accessible and clearly visible, whereby it is particularly easy to insert it into the hose element.

In the exemplary embodiment shown in FIGS. 26A to 26E, the (first) joint comprises at least a sleeve 85 which receives a pin 86 of the joint 54 in sections and rotatably mounts it. The sleeve 85 is fixedly and rigidly connected to the first of the two half shells 52. The joint 54 comprises at least one, for example two further sleeves 87 which also receive and rotatably mount said pin 86 in sections. The pin 86 extends along the first pivot axis.

The further (second) joint 84 comprises two sleeves 88 which are each fixedly and rigidly connected to the connector. A pin 89 extends, in each case in sections, through these sleeves 88 and is, for example, rotatably or non-rotatably mounted in them in each case. The 89 pin extends along the further (second) pivot axis. The pin 86 is, at one end 90 of this pin 86, connected to the pin 89 of the further (second) joint 84, for example fixedly and rigidly (alternatively rotatably). The (first) joint 54 as well as the two half shells 52, 53 is thus pivotable about the further (second) pivot axis, for example from the first position described above into the second position, and vice versa, by rotating the pin 89 of the further (second) joint 84.

In the exemplary embodiment shown in FIGS. 27A to 27D, the at least one joint 54 comprises a first joint 91 and a second joint 92. For example, the first joint 91 is arranged on a first side of the hollow body 8 and the second joint 92 is arranged on a second side of the hollow body 8 opposite to the first side. The first joint comprises, for example, a first pin 93 which is fixedly connected to the hollow body 8 on the first side of the hollow body 8 and is oriented parallel to the pivot axis of the at least one joint 54. The two half shells 52, 53 each have a first opening 94 through each of which the first pin 93 extends in sections. Accordingly, the second joint 92 has a second pin 94 which is fixedly connected to the hollow body 8 on the second side of the hollow body 8 and is oriented parallel to the (first) pivot axis. The half shells 52, 53 may each have a second opening 96 through each of which the second pin 94 extends in sections. The first pin 93 is rotatably mounted in the first openings 95. Accordingly, the second pin 94 is also rotatably mounted in the second openings 96. For example, the first pin 93 and the second pin 94 may be fixedly and rigidly connected to the hollow body, e.g. integrally.

The (first) pivot axis of the joint 54 extends within a plane which extends essentially perpendicular to the longitudinal axis of the hollow body 8 or perpendicular to the longitudinal axis of the hose element 9. In particular the (first) pivot axis can be oriented essentially perpendicular to the longitudinal axis of the hollow body 8 or (in the connected state) perpendicular to the longitudinal axis of the channel of the hose element. When the two half shells are pivoted apart, as is shown in FIGS. 27A and 27B, the perpendicular orientation of the (first) pivot axis allows for the hollow body to be particularly accessible and visible. The orientation of the (first) pivot axis relative to the hollow body 8 or to its longitudinal axis is fixed, as the first and second joint 91 and 92 are directly connected to the hollow body 8.

In comparison, in the exemplary embodiment shown in FIGS. 13 to 17, due to the releasability of the connector 54 from the hollow body, the pivot axis formed by the joint 54 is not fixed and, in the connected state, is oriented essentially parallel to the longitudinal axis of the hollow body of the longitudinal axis of the channel of the hose element.

In the exemplary embodiments shown in FIGS. 26A to 27A, just as in the exemplary embodiment shown in FIGS. 13 to 17, the connected state can be achieved without axial displacement of the connector, so that advantageously creasing of the hose element can be prevented or at least reduced. Additionally, a particularly good visual inspection of the hose element during connection is possible and, due to the fixed connection between the connector and the hollow body, an undesired release of the connector from the hollow body is impossible, while the connector in the exemplary embodiment shown in FIGS. 13 to 17 forms a unit which is detachable from the hollow body.

In the exemplary embodiments shown in FIGS. 26A to 27D, the connector additionally has a securing sleeve 96 which is axially movable relative to the two half shells 52, 53 of the connector between a first position, see FIGS. 26A to 26C or FIGS. 27A to 27B, and a second position, see FIGS. 26D to 26E or FIGS. 27C to 27D. The securing sleeve is designed to receive the two half shells 52, 53 of the connector 48 in the connected state of the cannula system 2 and to stabilize them in the closed configuration, when the securing sleeve is in the second position. For example, the securing sleeve 96 may have an inner contour 97, for example in the shape of an inwardly directed protrusion, and the hollow body 8 may have a corresponding outer contour 99, for example in the shape of a receptacle for the protrusion. It may, for example, be provided, that the outer contour is reciprocally engaged with the inner contour when the securing sleeve is in the second position, in order to axially stabilize the securing sleeve 97 there. Additionally, or alternatively, the securing sleeve 97 and the hollow body may have corresponding threads (inner thread, outer thread).

In the exemplary embodiments described based on FIGS. 11 to 25 and FIGS. 26A to 27D, it is further provided that the connector 48 comprises a region 59 that is configured, in the connected state of the cannula system 2, to push an axial section 60 of the hose element, which typically abuts the front end region 11 of the hose element 9, radially inwardly against a foremost edge 61 of the front edge region 15 of the hollow body 8 so as to prevent blood from penetrating between the outer surface 55 of the hollow body 8 and the inner surface 62 of the hose element 9 resting thereon.

In the exemplary embodiments described based on FIGS. 11 to 25 and FIGS. 26A to 27D, the connector 48 comprises a connecting element 63, and the hollow body 8 also comprises a connecting element 64. The connecting element 64 of the hollow body 8 is configured to establish a detachable connection to the connecting element 64 of the connector 48 in the connected state of the cannula system 2, so as to prevent undesirable axial displacement of the connector 48 relative to the hollow body 8, for example by way of form fit and/or force fit between these connecting elements 63, 64. In the examples of connectors 48 shown in FIGS. 13 to 25 and FIGS. 26A to 27D, the connecting elements 63 of the connector 48 each include at least one radially inwardly directed protrusion 65. The connecting elements 64 of the hollow bodies 8 of these examples include at least one receiving region 66 for the respective protrusion 65. In the examples shown in FIGS. 18 to 21 and 23, the connecting elements 63 of the respective connectors 48 comprise detent arms 67, which each include one of the radially inwardly directed protrusions 65. In the examples shown in FIGS. 22 and 24, the connecting elements 63 of the respective connectors 48 comprise a thread 68, and the connecting element 64 of the respective hollow body 8 comprises a corresponding mating thread 69.

In the exemplary embodiments shown based on FIGS. 11 to 17 and 24 to 25 and FIGS. 26A to 27D, the connector 48 includes at least one protrusion 80, in the form of a ridge, which protrudes radially into the interior region 51 and is configured to transmit the clamping forces onto the front end region 11 of the hose element 9. These protrusions 80 are each parts of the base body 49 of the connector 48. In the examples shown in FIGS. 11 to 17 and FIGS. 26A to 27D, the ridges extend circumferentially around the hose element 9. In the examples shown in FIGS. 14 and 15 and FIGS. 26A to 27D, the ridges extend in a pointed manner toward the inside. In the example shown in FIGS. 24 and 25, the ridges extend in the axial direction and taper radially inwardly.

In the exemplary embodiments shown based on FIGS. 18 to 25, the base body comprises multiple axial slots 82, which each extend through the region 59 and are thus disposed in the respective axial end regions of the base body 49. In this way, radial flexibility of the base body 49 can be increased in these end regions.

Advantageously, the cannula 7 has a particularly simple design in the cannula systems shown in FIGS. 11 to 25 and FIGS. 26A to 27D. For example, it is formed completely of the hose element 9, which in the simplest case can, in turn, be made entirely of the described graft material. It is thus possible that the cannula 7 does not comprise any tensioning elements or any reinforcing elements in the front end region thereof, which are fixedly connected to the front end region 11 of the hose element 9. The foremost end 13 of the hose element 9 can thus have been created, for example, in that the hose element has previously been shortened at the front end thereof by cutting. In the simplest case, the foremost end 13 can thus be a cut edge of the hose element 9 or a cut surface through the hose element 9.

All shown exemplary embodiments allow a connection between the respective cannula 7 and the respective hollow body 8 to be established easily and purely manually.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed. Unless otherwise indicated or the context suggests otherwise, as used herein, "a" or "an" means "at least one" or "one or more."

LIST OF REFERENCE NUMERALS 1 blood pump system
2 cannula system
3 blood pump
4 pump housing
5 pump inlet
6 pump outlet
7 cannula
8 hollow body
9 hose element
10 channel
11 front end region
12 receiving region
13 foremost end
14 inlet opening
15 front end region
16 stop
17 widening
18 surface
19 tension ring
20 axial overlapping region
21 surface
22 surface
23 surface
24 surface
25 foremost end
26 surface
27 intermediate space
28 sealing ring
29 rear end
30 rear end
31 surface
32 surface
33 axial overlapping region
34 operating element
35 base body
36 grip surface
37 interior region
38 receiving region
39 receiving region
40 detent element (detent arm)
41 detent tooth
42 mating detent element 43 detent surface
44 hole
45 sealing ring
46 pump chamber
47 outer wall
48 connector
49 base body
50 inner surface
51 interior region (cavity)
52 half shell
53 half shell
54 joint
55 surface
56 closure device
57 detent element
58 detent element
59 region
60 section
61 foremost edge
62 inner surface
63 connecting element
64 connecting element
65 protrusion
66 receiving region
67 detent arm
68 thread
69 mating thread
70 front opening
71 rear opening
72 surface
73 flexible element
74 clamping sleeve
75 wedge element
76 operating element
77 slot
78 slot
79 subregion
80 subregion
81 protrusion
82 slot
83 reinforcing sleeve
84 further joint
85 sleeve
86 pin
87 sleeve
88 sleeve
89 pin
90 end of the pin
91 first joint
92 second joint
93 first pin
94 second pin
95 first opening
96 second opening
97 securing sleeve
98 inner contour
99 outer contour

The invention claimed is:

1. A cannula system for conducting a liquid, in particular blood, comprising:
   a cannula comprising a hose element including a front end region and a rear end region, wherein a channel extends from the front end region of the hose element to the rear end region of hose element through the hose element;
   a hollow body, and in particular a tube or a further hose element, wherein the hollow body includes a front end region that can be inserted into the channel of the hose element through a front inlet opening of the channel; and
   a connector which is configured, in a connected state of the cannula system in which the front end region of the hollow body is inserted into the channel of the hose element of the cannula, to receive the front end region of the hose element and the front end region of the hollow body in an interior region of the connector, wherein the front end region of the hollow body and the connector are configured to exert clamping forces onto the front end region of the hose element in the connected state of the cannula system, and to clamp the front end region of the hose element between the front end region of the hollow body and the connector;
   wherein the connector comprises a clamping sleeve, the clamping sleeve being disposed in the interior region of the connector and configured, in the connected state of the cannula system, to enclose the front end region of the hose element and exert a clamping force of the connector on the front end region of the hose element;
   wherein the connector comprises a wedge element, the wedge element and the clamping sleeve being movable relative to one another between a preloaded configuration, in which the wedge element is disposed in a slot of the clamping sleeve and the clamping sleeve is preloaded and expanded by the wedge element, and a released configuration, in which the clamping sleeve is not preloaded and expanded by the wedge element, the wedge element and the clamping sleeve being in the released configuration when the cannula system is in the connected state.

2. The cannula system of claim 1 wherein the connector comprises a base body, which has a sleeve-shaped design and includes an inner surface which defines the interior region of the connector.

3. The cannula system of claim 1, wherein the connector comprises an operating element which can be moved between a first position and a second position, forms an outer operating surface of the connector, and is connected to the wedge element.

4. The cannula system of claim 1, wherein the clamping sleeve is mounted so as to be axially displaceable.

5. The cannula system of claim 1, wherein
   the hose element is made of a graft material or
   the front end region of the hose element is made of a graft material or
   a foremost edge of the hose element, which circumscribes the front inlet opening of the channel, is made of a graft material.

6. The cannula system of claim 1, wherein the graft material of the hose element is formed by a tubular woven fabric structure, which is preferably provided with a coating.

7. The cannula system of claim 5, wherein the graft material of the hose element, in the connected state of the cannula system, directly abuts an outer surface of the hollow body.

8. The cannula system of claim 5, wherein the graft material of the hose element, in the connected state of the cannula system, directly abuts an inner surface of the connector.

9. The cannula system of claim 1, wherein the cannula
   does not comprise any reinforcing element for strengthening or stabilizing the hose element and/or
   does not comprise any tensioning elements for axially or radially tensioning the hose element.

10. The cannula system of claim 1, wherein, in a basic state of the hose element, in which the front end region of the hollow body is not pushed into the channel of the hose element, a diameter of the front inlet opening of the channel is greater than an outside diameter of the foremost edge of the front end region of the hollow body.

11. The cannula system of claim 1, wherein the hollow body has a higher strength than the hose element.

12. The cannula system of claim 1, wherein the hollow body is made entirely or at least in some regions of a metallic material, such as stainless steel or titanium, and/or
   is made entirely or at least in some regions of a polymer, such as a silicone.

13. A blood pump system comprising a blood pump and a cannula system of claim 1, wherein the blood pump comprises a pump housing having a pump inlet and a pump outlet, the hollow body of the cannula system forming the pump outlet or the pump inlet of the blood pump.

* * * * *